United States Patent
Kim et al.

(10) Patent No.: US 6,730,419 B2
(45) Date of Patent: May 4, 2004

(54) BLUE LIGHT EMITTING COMPOUND AND ORGANIC ELECTROLUMINESCENT DEVICE EMPLOYING THE SAME AS COLOR DEVELOPING SUBSTANCE

(75) Inventors: Geon-Hee Kim, Suwon (KR); Sung-Han Kim, Seoul (KR); Soon-Ki Kwon, Jinju (KR); Yun-Hi Kim, Jinju (KR); Dong-Cheol Shin, Geochang-gun (KR); Hyung-Sun Kim, Hamyang-gun (KR); Hyun-Cheol Jeong, Hadong-gun (KR)

(73) Assignee: Samsung SDI Co., Ltd., Suwon (KR)

( * ) Notice: Subject to any disclaimer, the term of this patent is extended or adjusted under 35 U.S.C. 154(b) by 0 days.

(21) Appl. No.: 10/187,725

(22) Filed: Jul. 1, 2002

(65) Prior Publication Data

US 2003/0064246 A1 Apr. 3, 2003

(30) Foreign Application Priority Data

Aug. 13, 2001 (KR) ........................ 2001-48824

(51) Int. Cl.[7] ..................... H05B 33/14; C09K 11/06
(52) U.S. Cl. ................. 428/690; 428/917; 313/504; 252/301.16
(58) Field of Search ................. 428/690, 917; 313/504; 252/301.16

(56) References Cited

U.S. PATENT DOCUMENTS

2002/0058156 A1 * 5/2002 Toguchi et al. ............. 428/690

FOREIGN PATENT DOCUMENTS

| EP | 0 388 768 A3 |   | 9/1990 |
| EP | 0 388 768 A2 |   | 9/1990 |
| EP | 0 388 768 B1 |   | 9/1990 |
| EP | 0 866 645 A1 |   | 9/1998 |
| EP | 0 949 696 A2 | * | 10/1999 |
| JP | 08-012969 | * | 1/1996 |
| JP | 08-333283 | * | 12/1996 |
| JP | 08-333569 | * | 12/1996 |
| JP | 10-110163 | * | 4/1998 |
| JP | 10-261488 |   | 9/1998 |
| JP | 2000-053677 | * | 2/2000 |
| JP | 2000-143569 | * | 5/2000 |
| JP | 2000-191560 | * | 7/2000 |
| JP | 2001-335516 | * | 12/2001 |

OTHER PUBLICATIONS

T. Tsutsui et al, "Significance of multilayer structures in organic thin–film electroluminescent devices"; SPIE vol. 1910, pp. 180–189.
C.W. Tang et al, "Organic electroluminescent diodes" Appln. Phys. Lett. 51 (12), Sep. 21, 1987, pp. 913–915.

* cited by examiner

Primary Examiner—Cynthia H. Kelly
Assistant Examiner—Dawn Garrett
(74) Attorney, Agent, or Firm—Christie, Parker & Hale, LLP

(57) ABSTRACT

A blue light emitting compound and an organic electroluminescent device using the same are provided. The blue light emitting compound is represented by the following Formula 1, thereby providing an organic electroluminescent device having superior color purity.

Formula 1

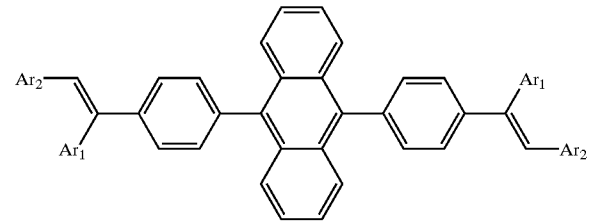

wherein $Ar_1$ and $Ar_2$ are each independent substituents or substituent groups selected from the group consisting of aryl groups on which an aryl group, an alkyl group or an alkoxy group having 5 to 30 carbons may be substituted; fused aromatic ring groups having 4 to 24 carbons, such as naphthalene and anthracene; aryl groups having 5 to 20 carbons as well as an alkyl amino group or an aryl amino group of 4 to 25 carbons; carbazole derivatives having an alkyl group or aryl group of 1 to 25 carbons; fluorenyl groups having a substituent on the C-9 position of the fluorenyl group selected from the group consisting of alkyl groups having 2 to 30 carbons, polyalkoxide groups, and alkyl or alkoxy substituted aryl groups; and aryl groups comprising a silyl group having a substituent selected from the group consisting of alkyl groups of 4 to 35 carbons, aryl groups, and alkyl or alkoxy substituted aryl groups.

8 Claims, 4 Drawing Sheets

BLUE LIGHT EMITTING COMPOUND AND ORGANIC ELECTROLUMINESCENT DEVICE EMPLOYING THE SAME AS COLOR DEVELOPING SUBSTANCE

CROSS-REFERENCE TO RELATED APPLICATION

This application claims priority of Korean Patent Application No. 2001-48824 filed on Aug. 13, 2001, under 35 U.S.C. § 119, the entire disclosure of which is hereby incorporated by reference.

FIELD OF THE INVENTION

The present invention relates to a blue light emitting compound for organic electroluminescence and an organic electroluminescent device using the same, more particularly, to a blue light emitting compound useful in an organic electroluminescent device which is an emissive display device and has a wider viewing angle, a superior contrast ratio and a faster response time, and an organic electroluminescent device using the same.

BACKGROUND OF THE INVENTION

An electroluminescent (hereinafter referred to as "EL") device has several advantages, including a wider viewing angle, a superior contrast ratio and a faster response time as an emissive display device.

EL devices are classified as inorganic EL devices and organic EL devices based on the material used for forming an emitting layer, wherein the organic EL device has superior luminance, driving voltage and response speed properties compared to the inorganic EL device and can be polychromed.

An ordinary organic EL device has a structure in which an anode is formed on the upper part of a substrate, and a hole transport layer, a light-emitting layer, an electron transport layer and a cathode are sequentially formed on the upper part of the anode, wherein the hole transport layer, the light-emitting layer, and the electron transport layer are organic thin films comprising organic compounds.

The operating principle of the organic EL device having the structure as described above is as follows.

A hole injected from the anode is transferred to the light-emitting layer via the hole transport layer when a voltage is applied between the anode and the cathode. On the other hand, electrons are injected into the light-emitting layer via the electron transport layer from the cathode, and carriers are recombined with each other in the region of the light-emitting layer, thereby producing exitons. The exitons are changed into the ground state from the exited state, fluorescent molecules of the light-emitting layer emit light due to the change of state, and an image is formed.

On the other hand, Eastman Kodak company has developed an organic electroluminescent device using a low molecular aromatic diamine and an aluminum complex as a material for forming the light-emitting layer for the first time in 1987 (Appl. Phys. Lett. 51, 913, 1987).

Although compounds such as diphenylanthracene, tetraphenylbutadiene, and distyrylbenzene derivatives are developed as a blue light emitting material, it is known that the compounds tend to be easily crystallized due to the poor stability of the thin film. Idemitsu Company has developed a diphenyldistyryl based blue light emitting material in which the crystallization of the compounds is hindered by the branch phenyl group so that the thin film stability is improved [H. Tikailin, H. Higashi, C. Hosokawa, EP 388, 768(1990)], and Kyushu University has developed a distyrylanthracene derivative in which the thin film stability is improved by having electron withdrawing groups and electron donating groups [PRO. SPIE, 1910, 180(1993)].

Furthermore, it is disclosed in Japanese Patent Laid-open Publication No. Heisei 10-261488 that the life cycle can be lengthened by using a distyrylarylene derivative, the electron affinity of which is between 2.6 and 3.2 electron volts(eV), as a blue light emitting compound, thereby improving the thin film stability.

However, since these compounds have lower light emitting efficiencies compared to other colored light emitting compounds and there is a further need to improve the thin film stability, it is urgently required to develop a new blue light emitting compound so as to develop a blue light emitting device or a full color light emitting device.

SUMMARY OF THE INVENTION

In order to solve the foregoing problems, it is an object of the present invention to provide a new blue light emitting compound in which light emitting efficiency properties are improved.

It is another object of the present invention to provide an organic electroluminescent device which employs the new blue light emitting compound as a color developing substance.

DETAILED DESCRIPTION OF PREFFERED EMBODIMENTS

Figure 1:
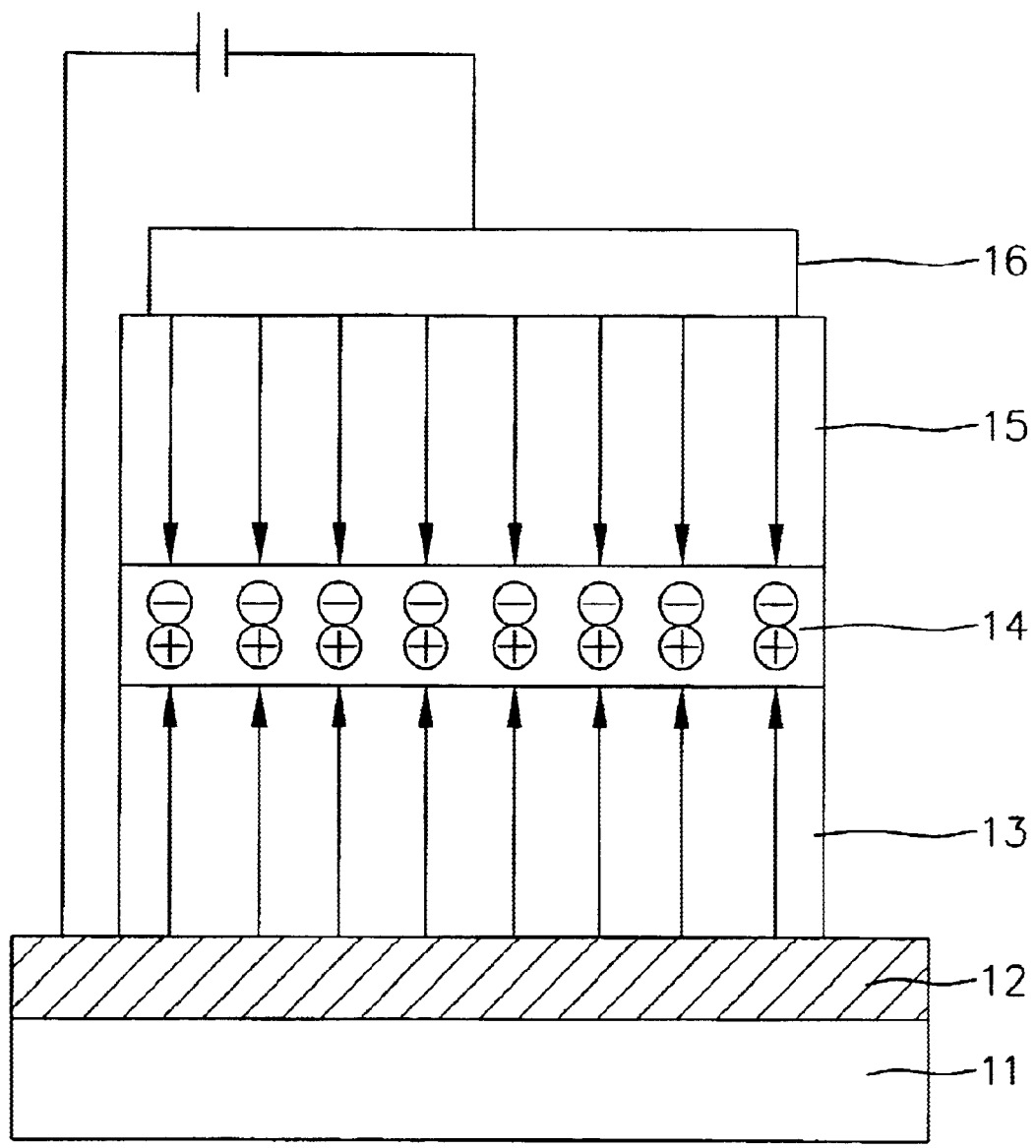
FIG. 1 is a schematic cross-sectional view showing the structure of an ordinary organic electroluminescent device which is manufactured in the order of a substrate, an anode, a hole transport layer, an emitting layer, an electron transport layer and a cathode.

In order to accomplish the objects, the present invention provides a blue light emitting compound represented by the following Formula 1

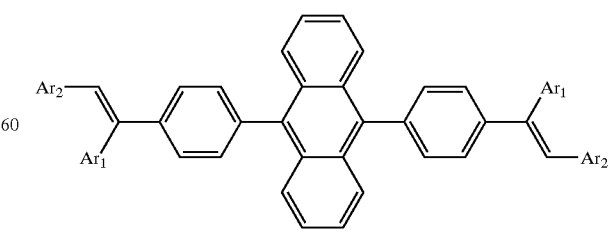

wherein $Ar_1$ and $Ar_2$, each of which are respectively independent substituents or substituent groups, are each selected from the group consisting of aryl groups on which an aryl group, an alkyl group or an alkoxy group having 5 to 30 carbons may be substituted; fused aromatic ring groups having 4 to 24 carbons, such as naphthalene and anthracene; aryl groups having 5 to 20 carbons as well as an alkyl amino group or an aryl amino group of 4 to 25 carbons; carbazole derivatives having an alkyl group or aryl group of 1 to 25 carbons; fluorenyl groups having a substituent on the C-9 position of the fluorenyl group selected from the group consisting of alkyl groups of 2 to 30 carbons, polyalkoxide groups, and alkyl or alkoxy substituted aryl groups; and aryl groups comprising a silyl group having a substituent selected from the group consisting of alkyl groups of 4 to 35 carbons, aryl groups, and alkyl or alkoxy substituted aryl groups.

A compound of the above Formula 1 according to the present invention, a material having 9,10-diphenylanthracene, has superior color purity as a blue light emitting material or a light emitting material having superior hole-transport capability, and is useful as a color developing substance for a display device. Furthermore, an organic electroluminescent device according to the present invention forms an organic film such as an emitting layer using a compound of the Formula 1, and improves the luminance properties compared to the use of an ordinary blue light emitting compound.

A blue light emitting compound according to the present invention is described in detail as follows.

Preferred compounds according to the invention comprising an aryl group of 5 to 30 carbons or an alkyl or alkoxy group substituted aryl group include:

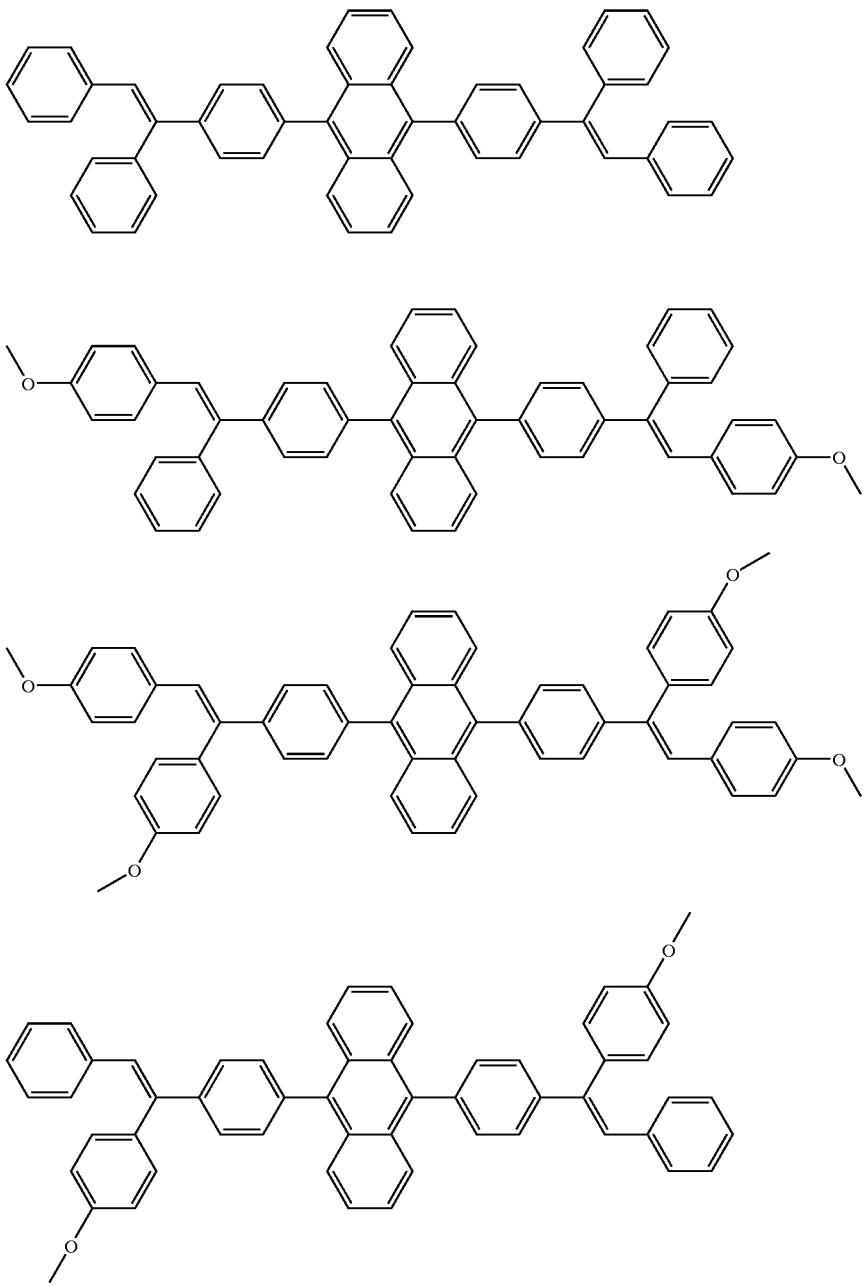

-continued
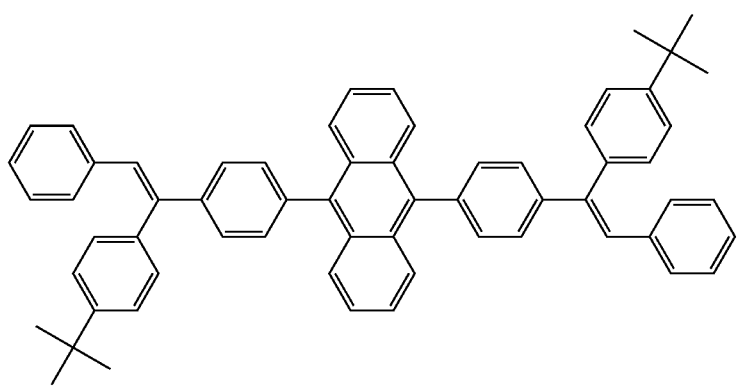
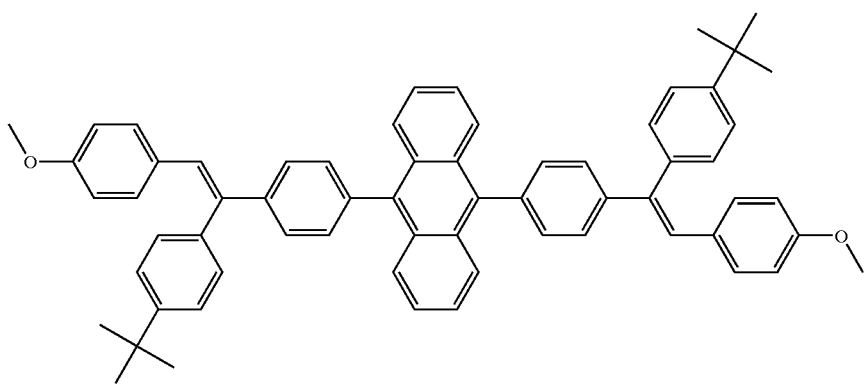
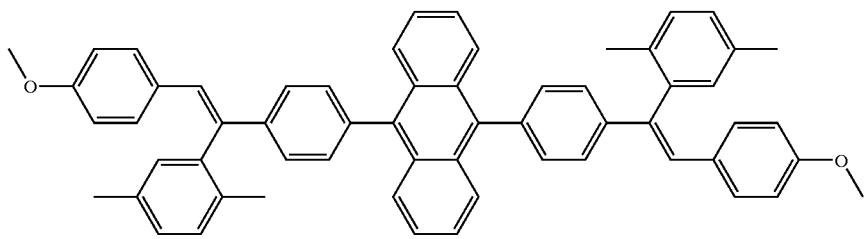
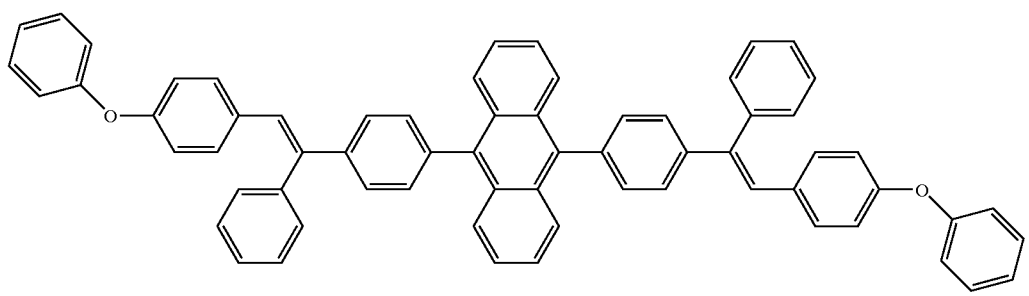
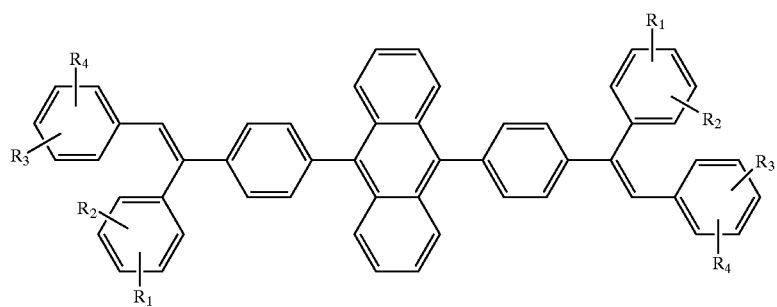

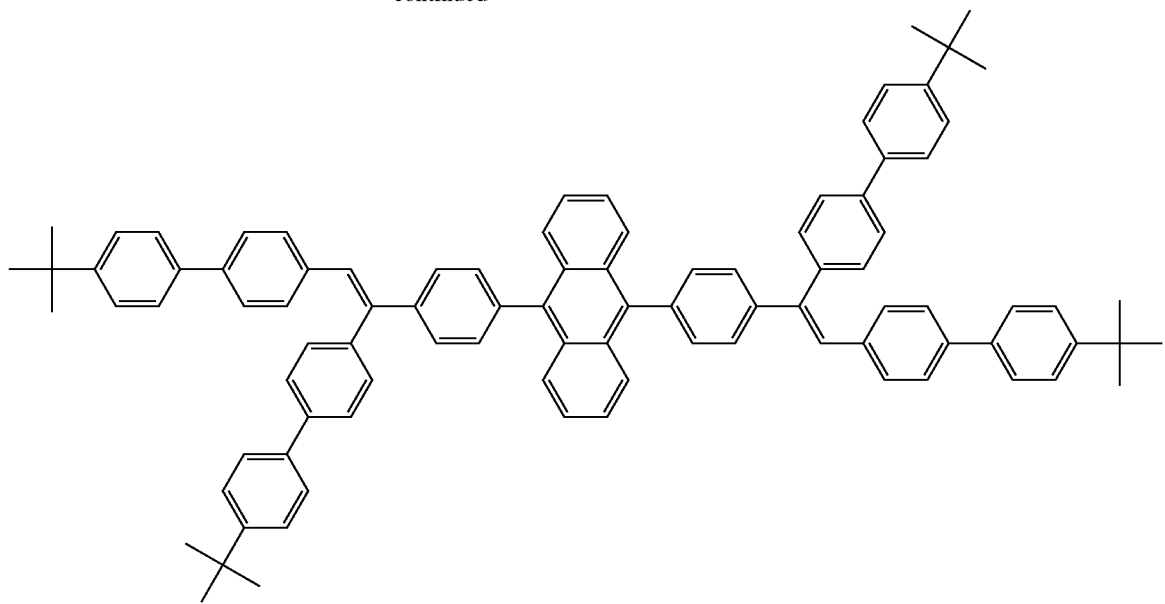
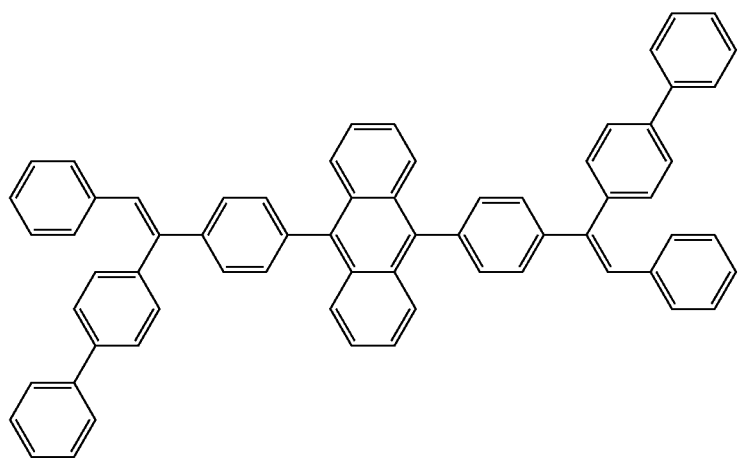
and
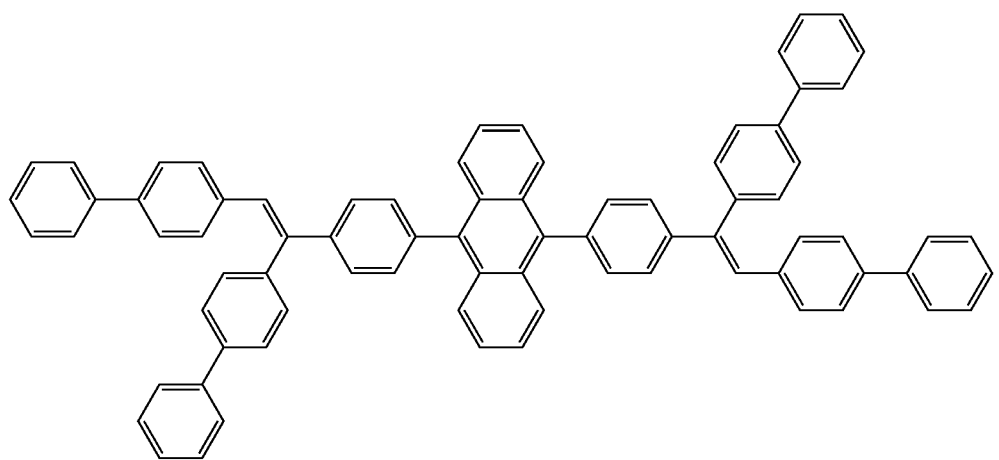

wherein $R_1$, $R_2$, $R_3$ and $R_4$ are each independently a substituent selected from the group consisting of hydrogen, alkyl groups having 1 to 25 carbons, alkoxy groups, and alkyl or alkoxy substituted aryloxy groups.
Preferred blue light emitting compounds having fused aromatic ring groups of 4 to 24 carbons, such as naphthalene and anthracene, include:
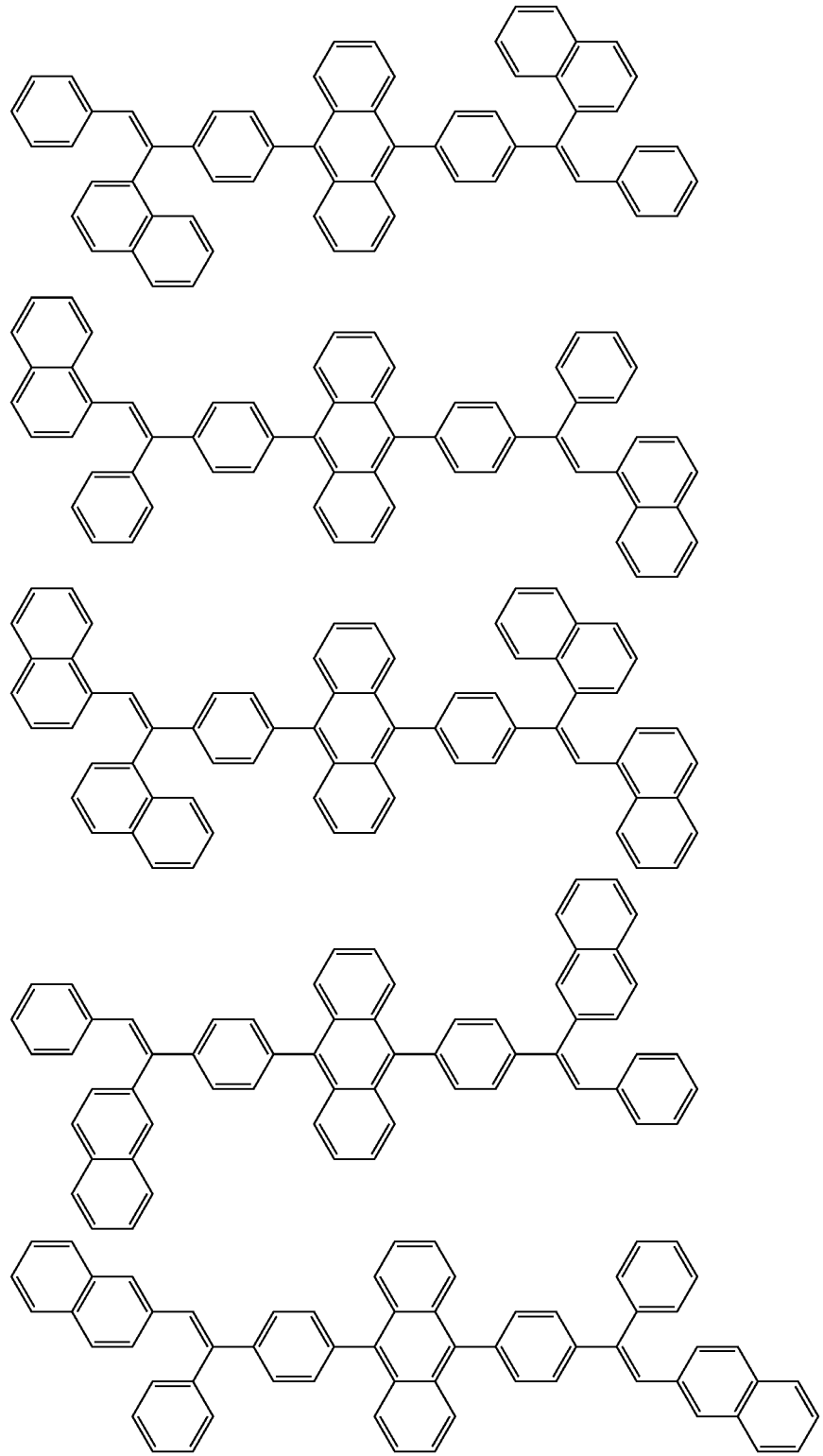
and

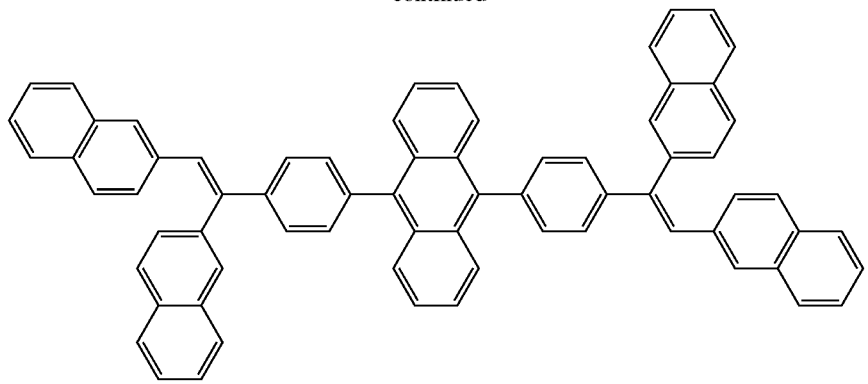
Preferred blue light emitting compounds with aryl groups having 5 to 20 carbons as well as an alkyl amino group or an aryl amino group of 4 to 25 carbons include:
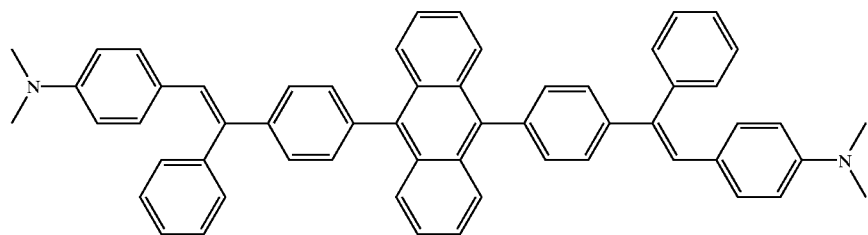
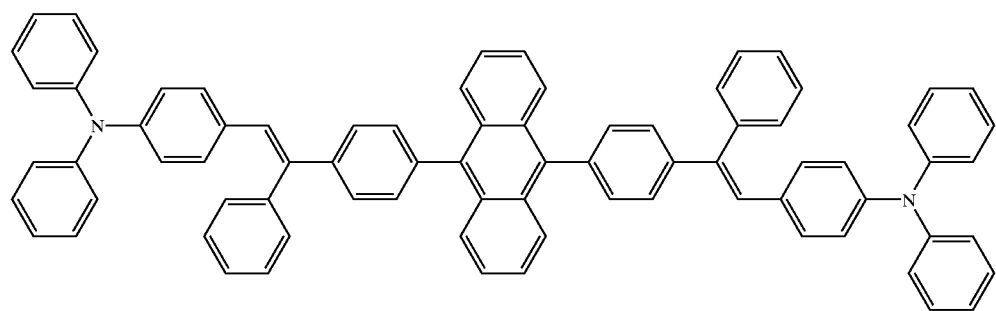
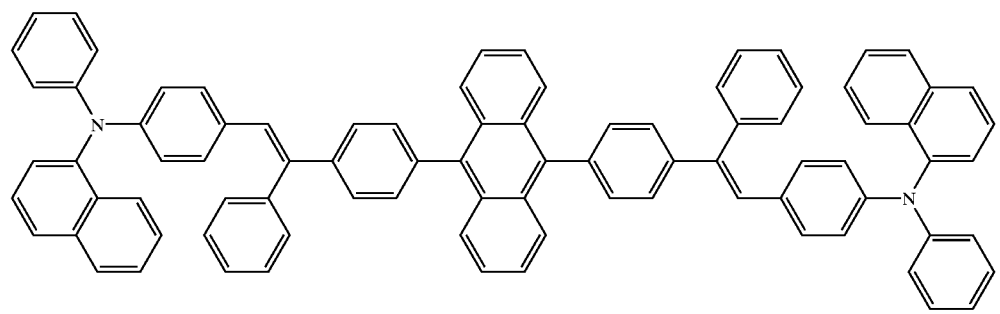

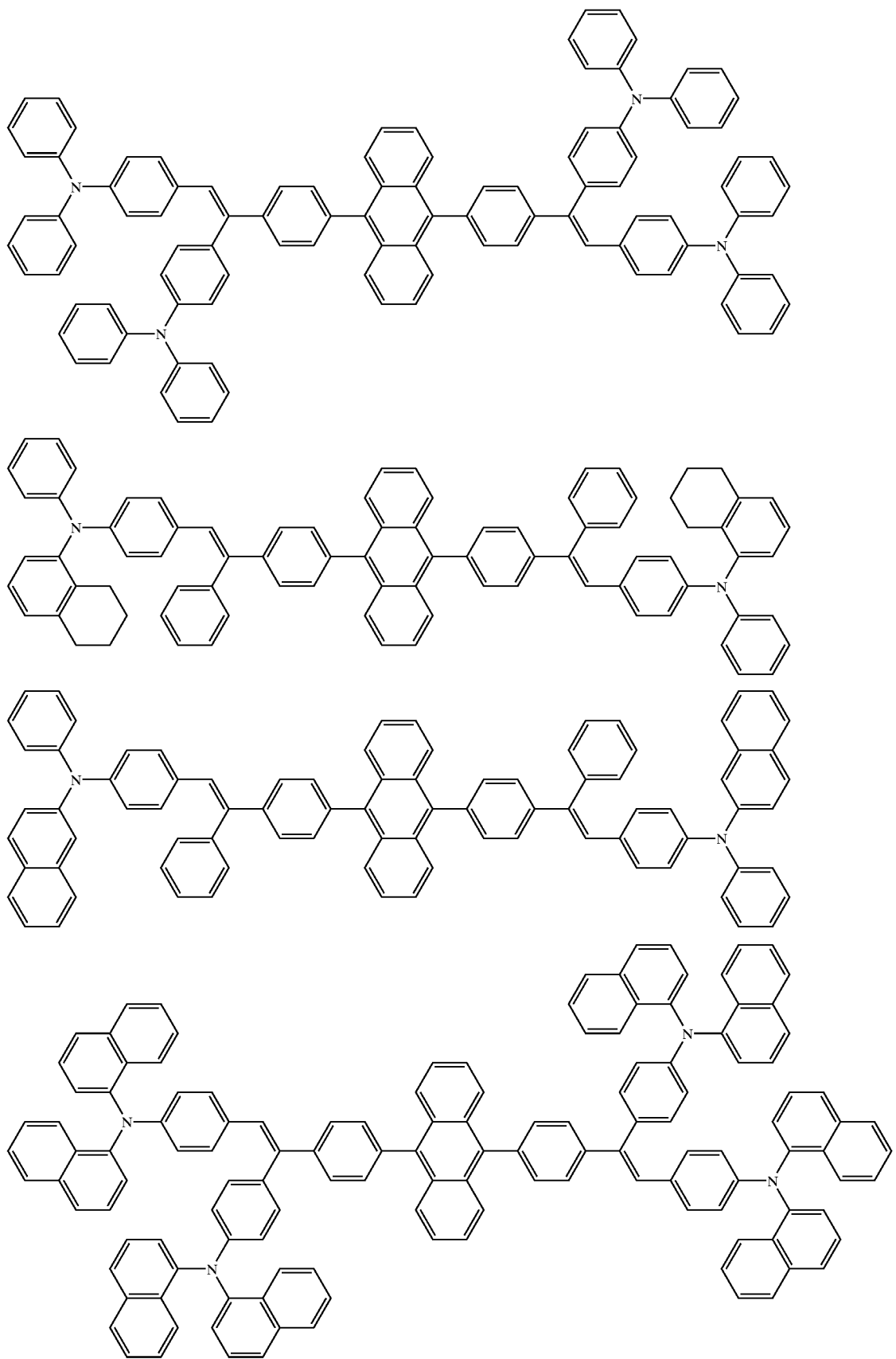

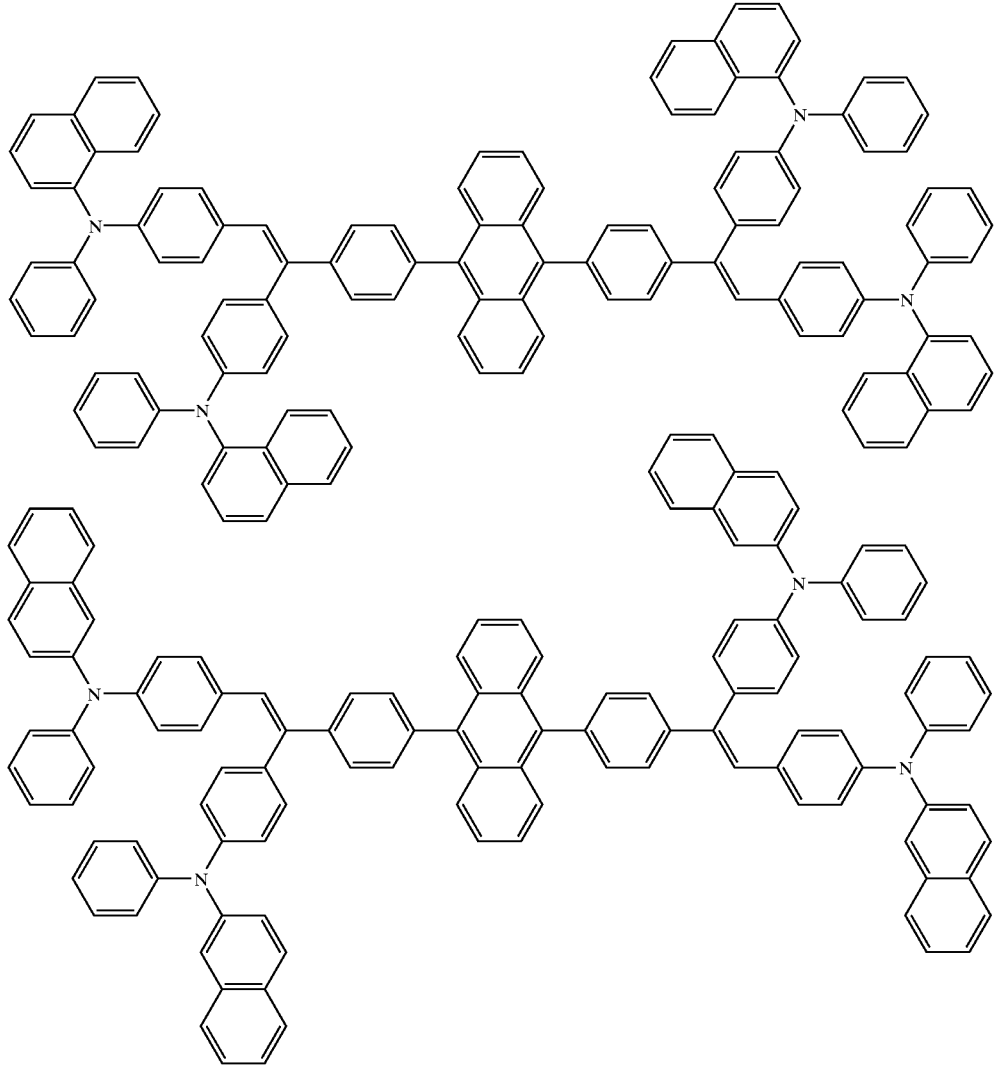
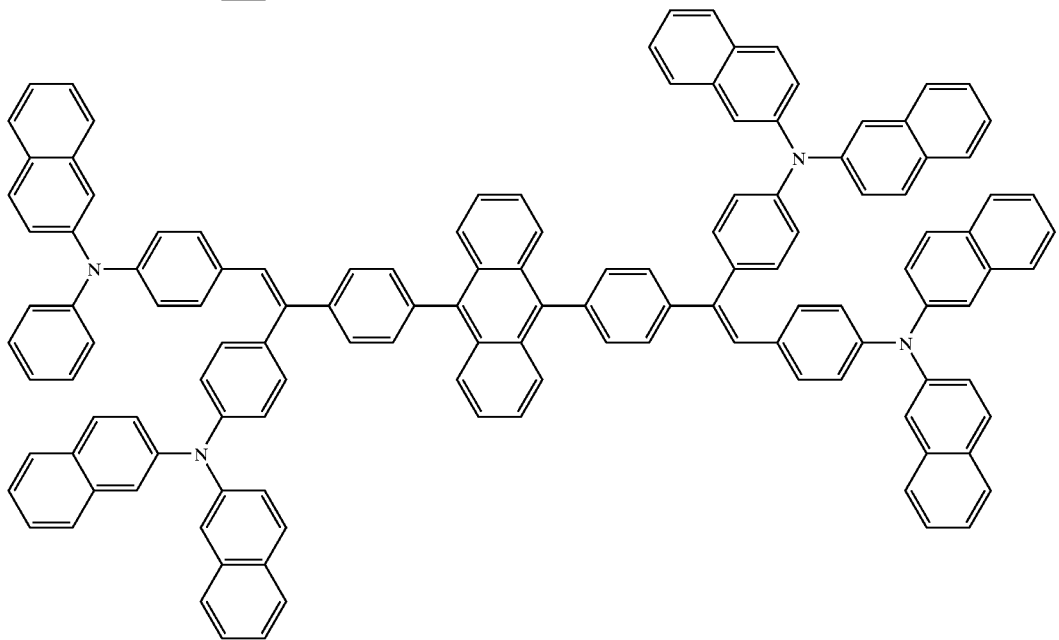
and

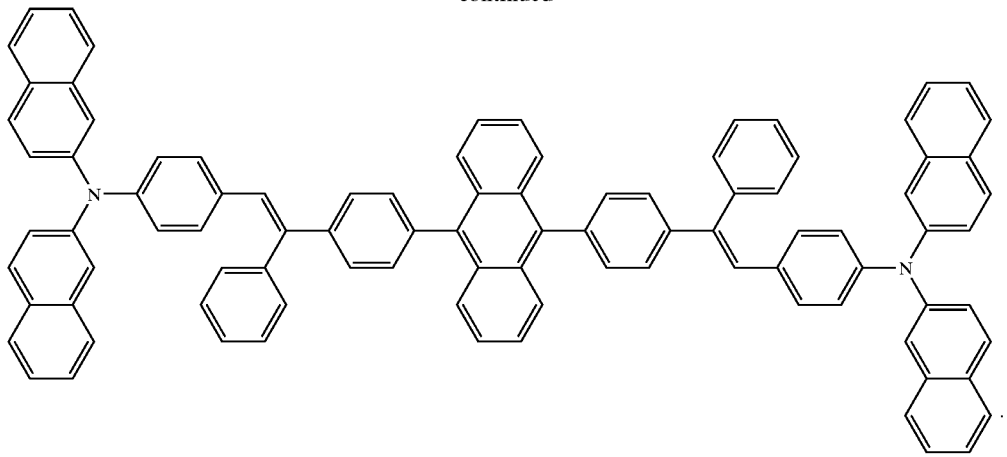
20
Preferred blue light emitting compounds with carbazole derivatives having an alkyl group or an aryl group of 1 to 25 carbons include:
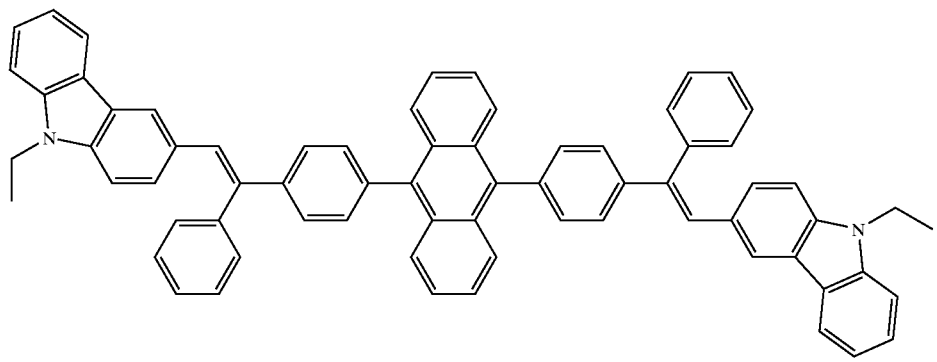
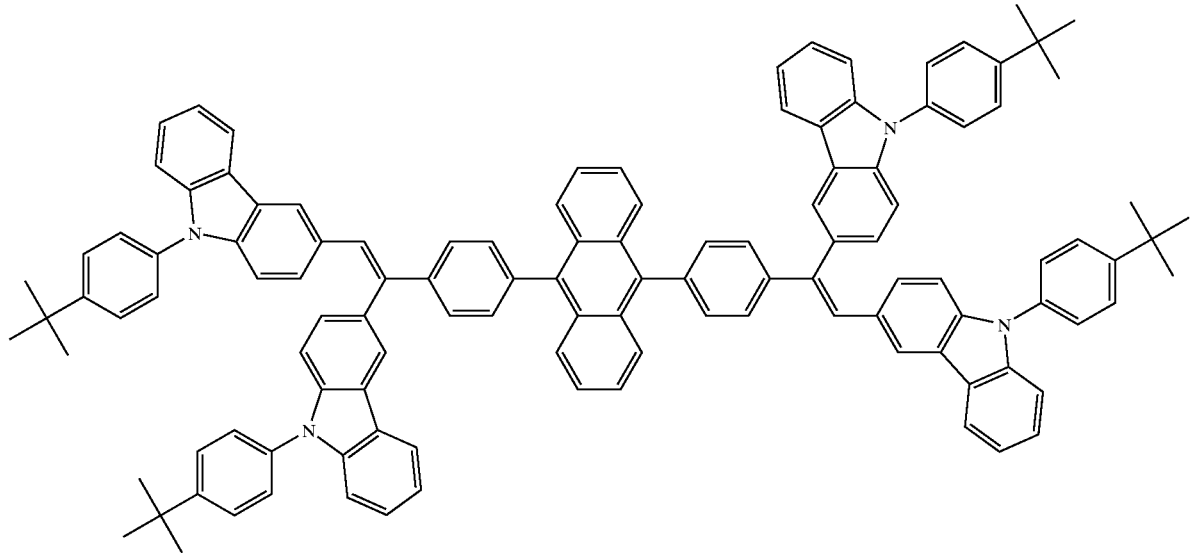

-continued
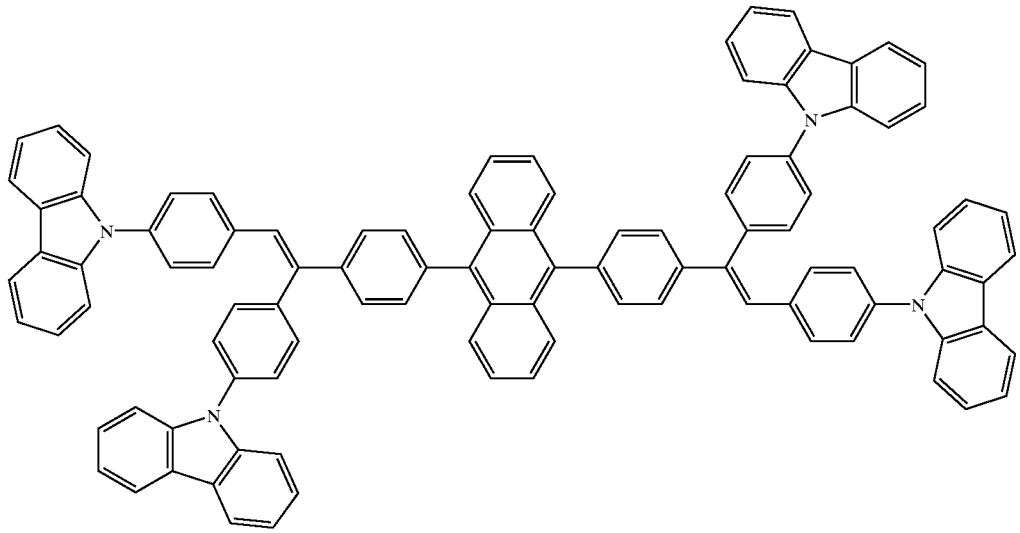
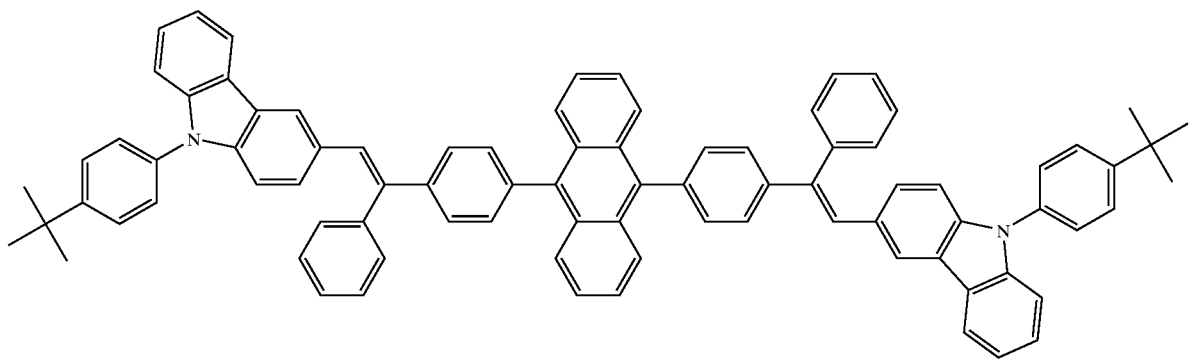
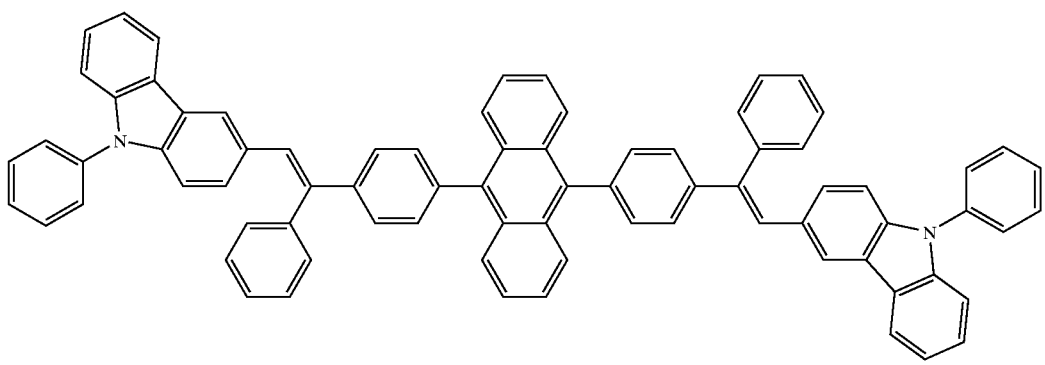
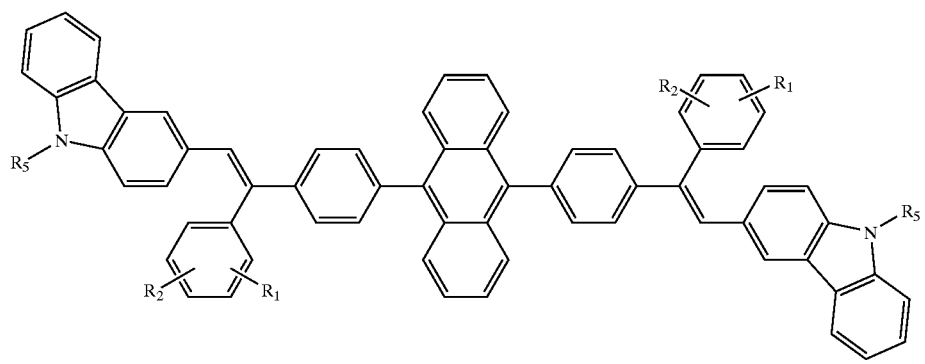

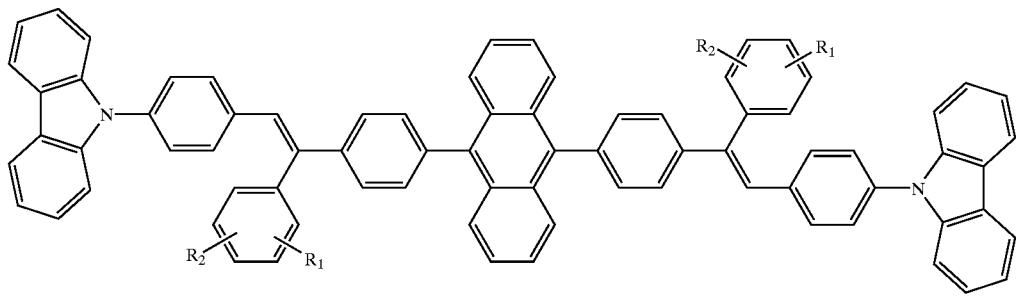
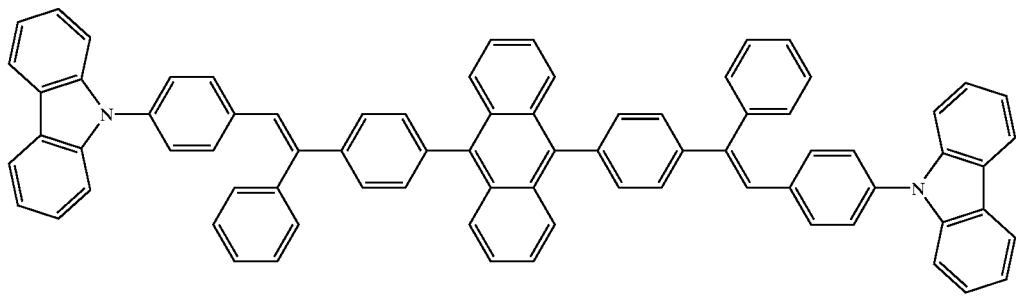
and
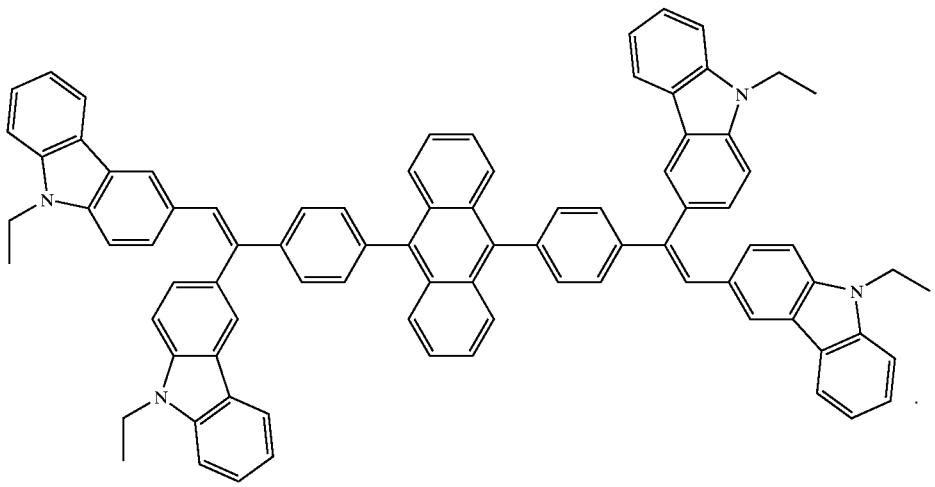
wherein $R_1$, $R_2$, and $R_5$ are each independently a substituent selected from hydrogen, alkyl groups having 1 to 25 carbons, alkoxy groups, and alkyl or alkoxy substituted aryloxy groups.
Preferred blue light emitting compounds with fluorenyl groups having a substituent on the C-9 position of the fluorenyl group selected from the group consisting of alkyl groups of 2 to 30 carbons, polyalkoxide groups, and alkyl or alkoxy substituted aryl groups include:
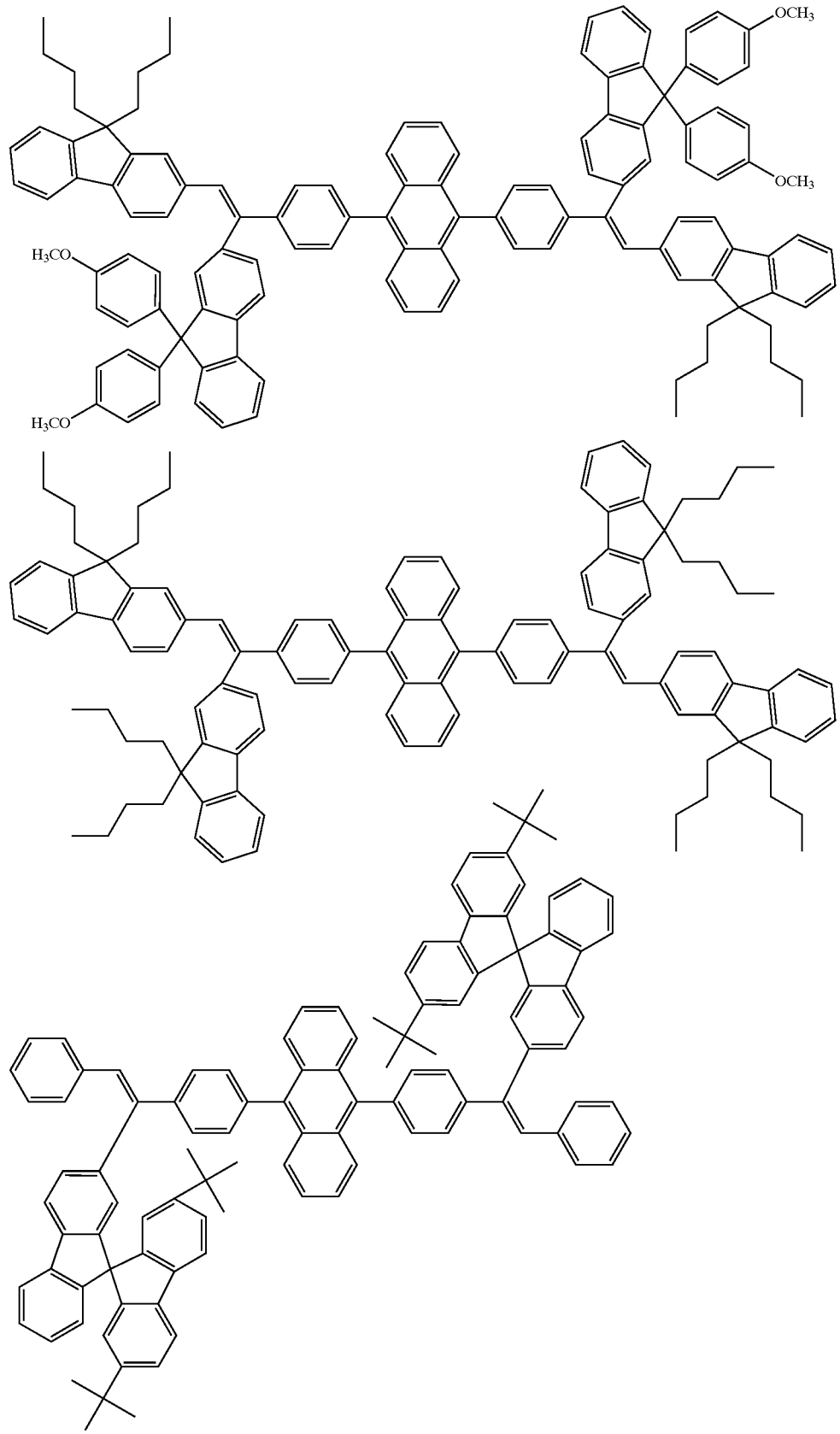

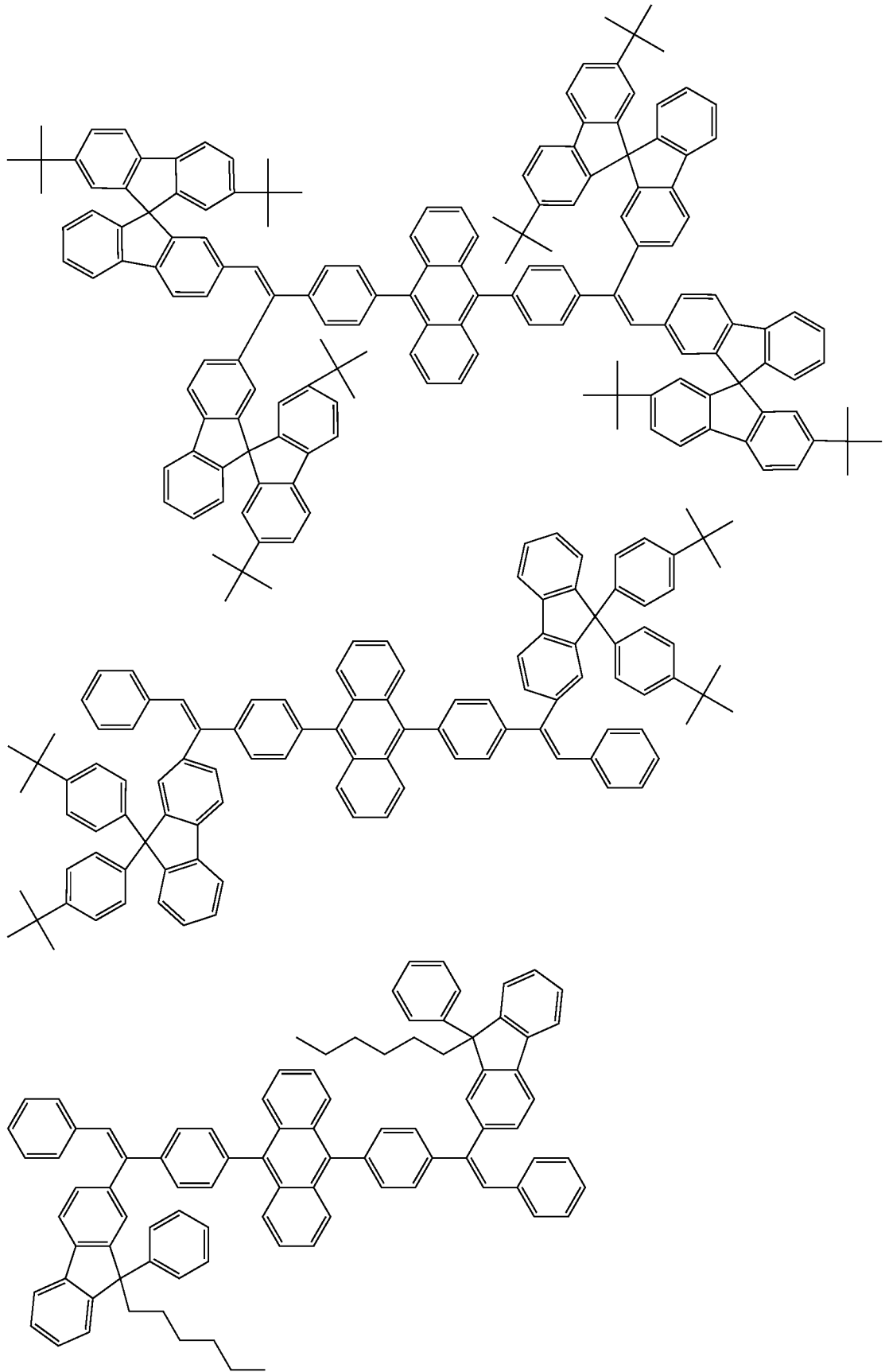

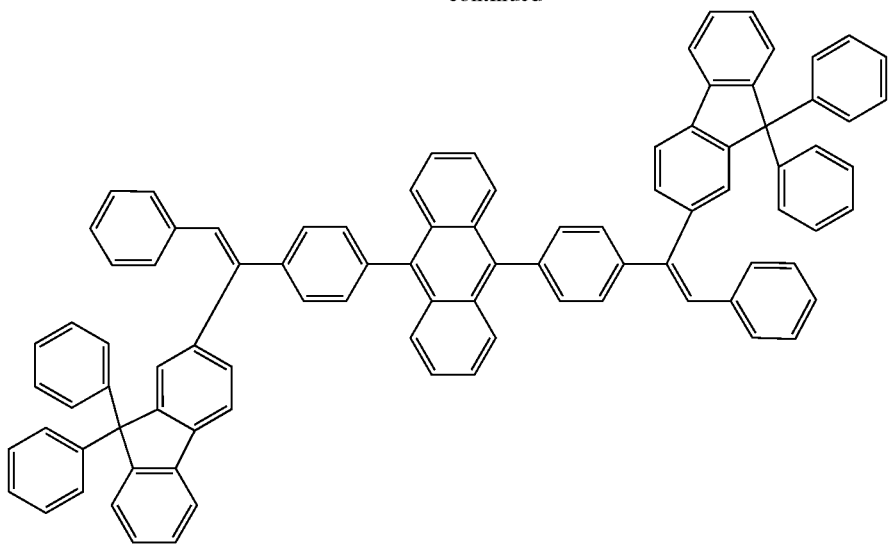
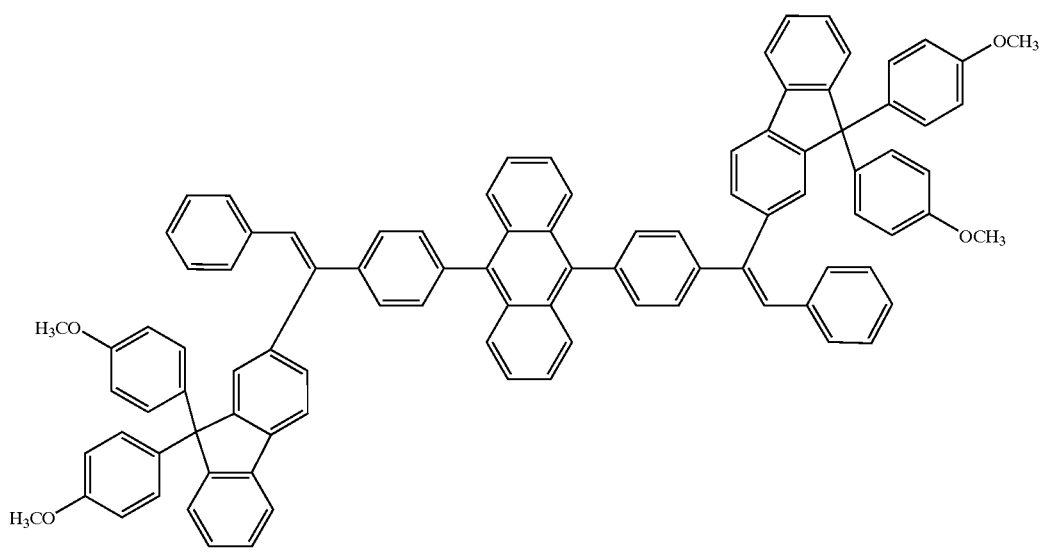
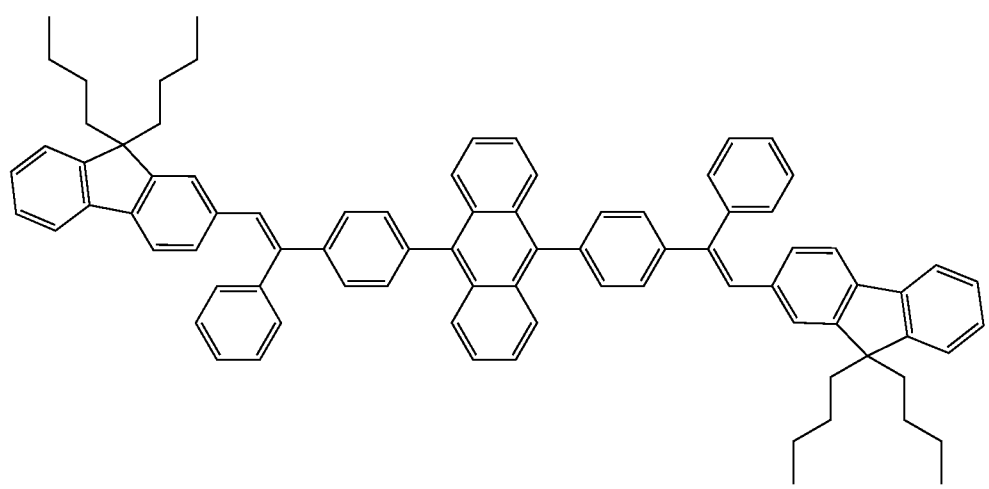

-continued
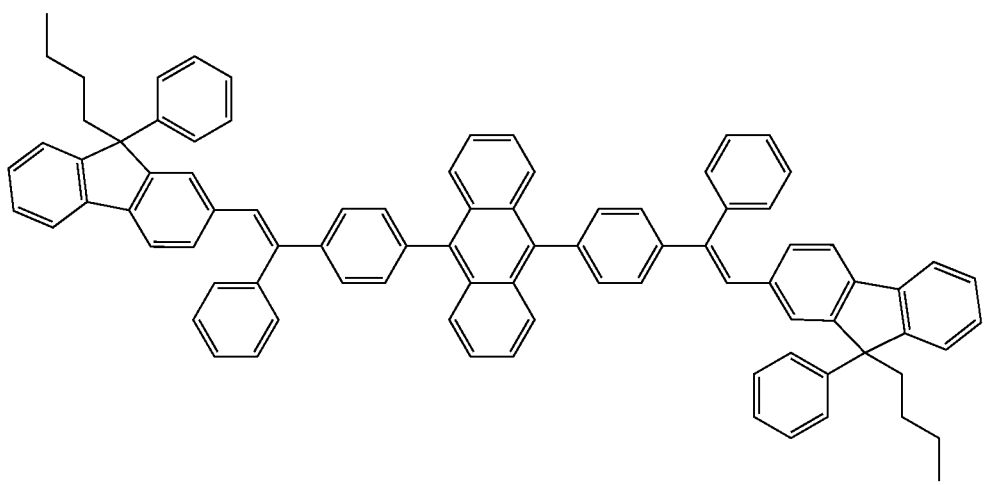
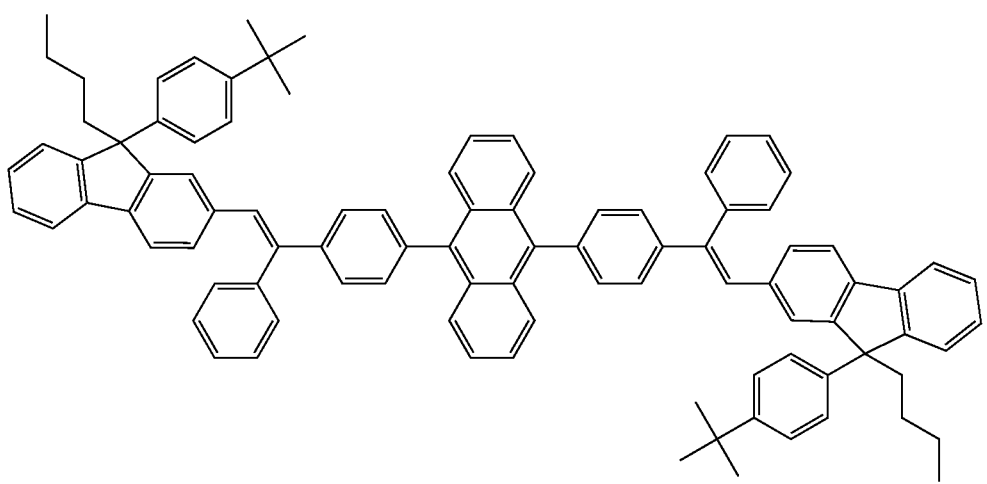
and
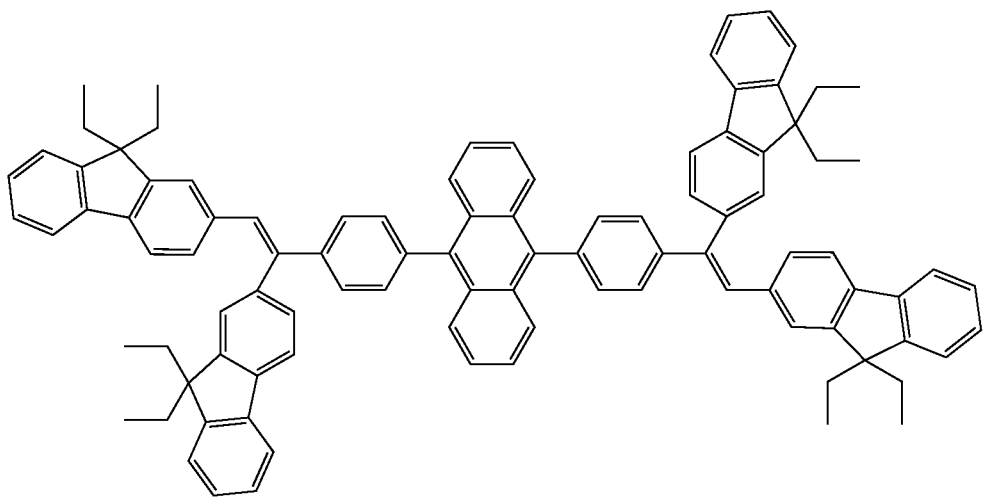

Preferred blue light emitting compounds having aryl groups with a silyl group substituted with a substituent selected from the group consisting of alkyl groups having 4 to 35 carbons, aryl groups, alkyl or alkoxy substituted aryl groups include:
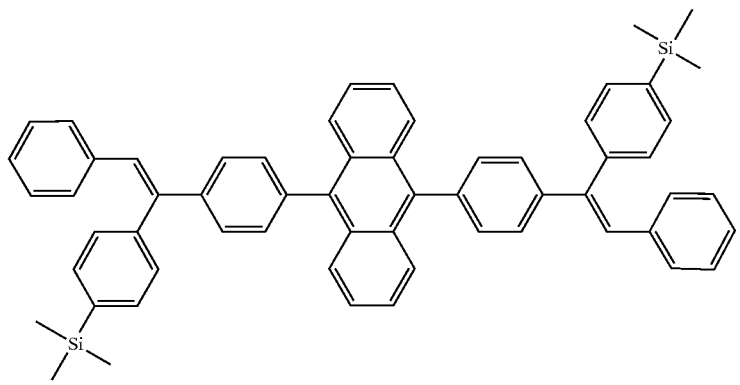
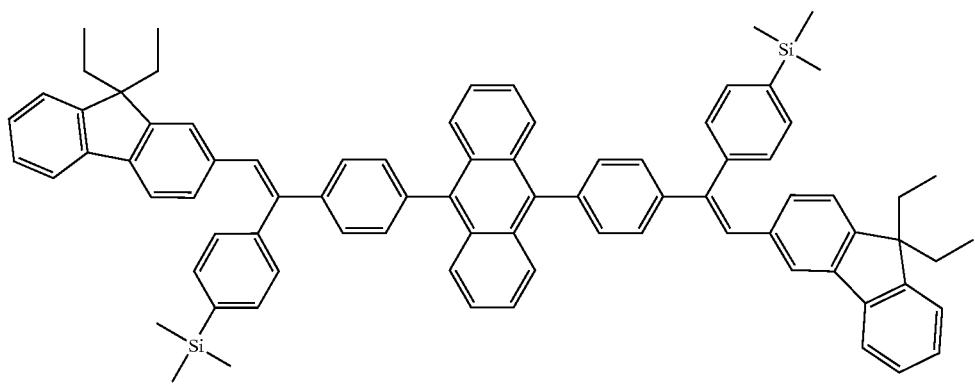
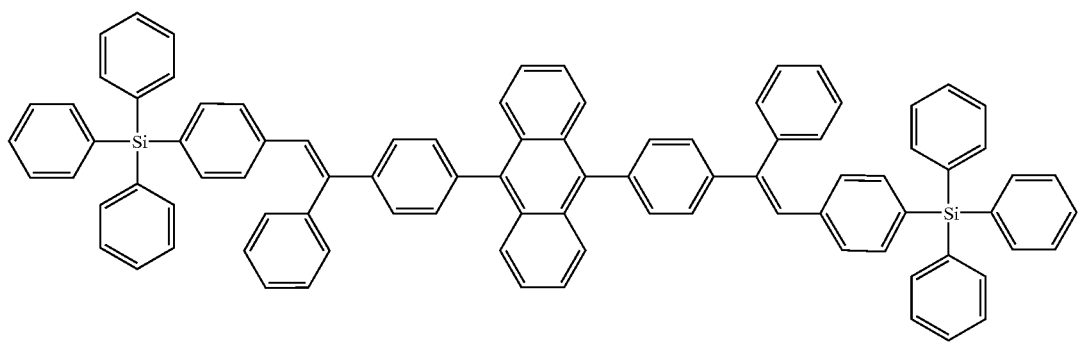
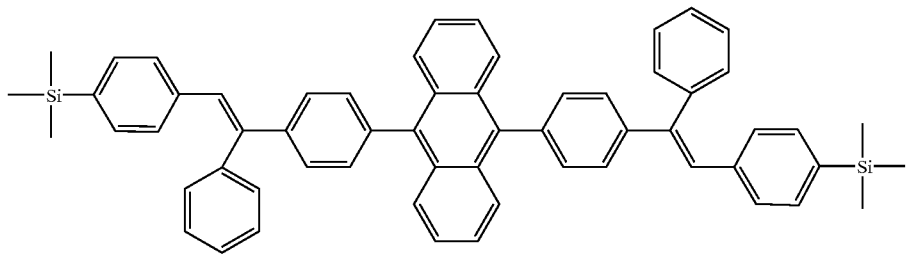
and -continued
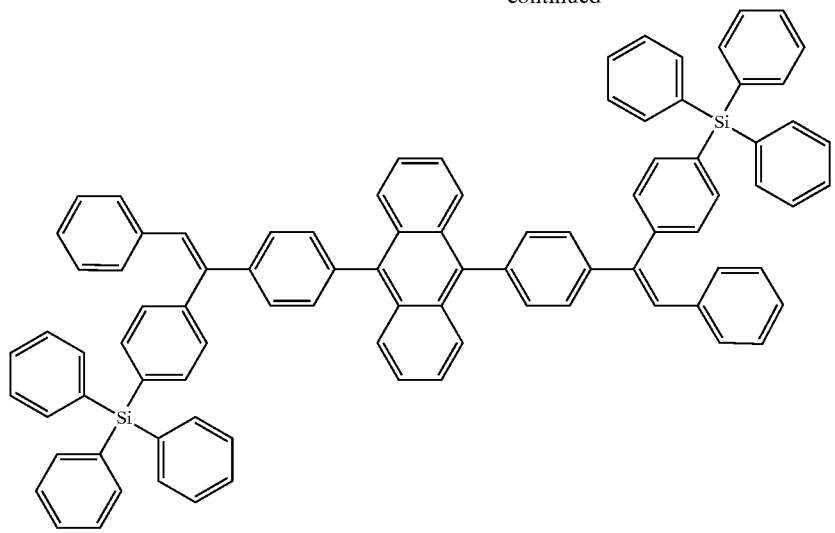
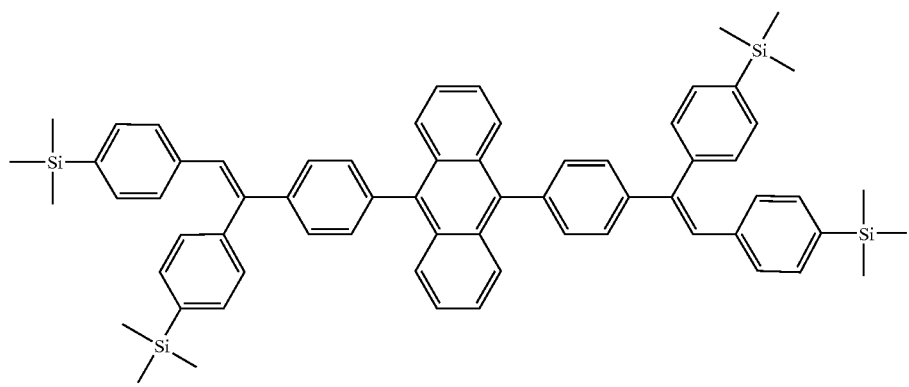
and
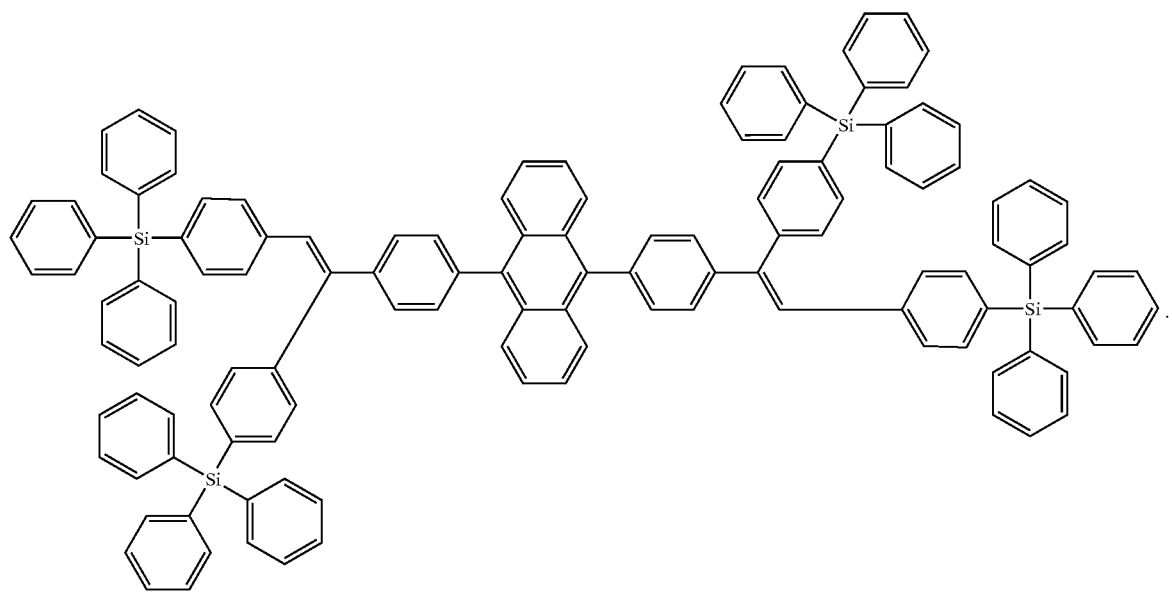

The second object of the present invention is achieved by a display device in which a light emitting compound having 9,10-diphenylanthracene is employed as a color developing substance. In a preferred embodiment of the present invention, an organic electroluminescent device employing a light emitting compound having 9,10-diphenylanthracene as a color developing substance is provided.

In an organic electroluminescent device comprising an organic film formed between a pair of electrodes, a second object of the present invention is to provide an organic electroluminescent device in which the organic film comprises a blue light emitting compound of the following Formula 1:

Formula 1

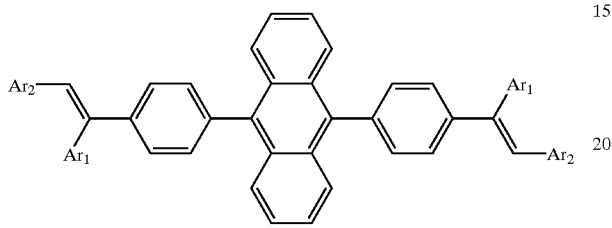

wherein $Ar_1$ and $Ar_2$ are each substituents independently selected from the following structures:

Group 1: aryl groups in which an aryl group, an alkyl group or an alkoxy group with 5 to 30 carbons is substituted;

Group 2: fused aromatic ring groups having 4 to 24 carbons, such as naphthalene and anthracene;

Group 3: aryl groups having 5 to 20 carbons as well as an alkyl amino group or an aryl amino group with 4 to 25 carbons;

Group 4: carbazole derivatives having an alkyl group or aryl group with 1 to 25 carbons;

Group 5: fluorenyl groups having one substituent on the C-9 position of the fluorenyl group selected from alkyl groups having 2–30 carbons, polyalkoxide groups, and alkyl or alkoxy substituted aryl groups; and Group 6: aryl groups comprising a silyl group substituted with a substituent selected from the group consisting of alkyl groups with 4 to 35 carbons, aryl groups, and alkyl or alkoxy substituted aryl groups.

Preferred blue light emitting compounds of the Formula 1 according to the present invention are represented by the following Formulae 2a to 2f:

Formula 2a

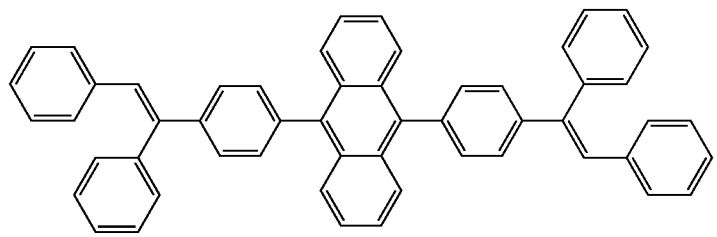

Formula 2b

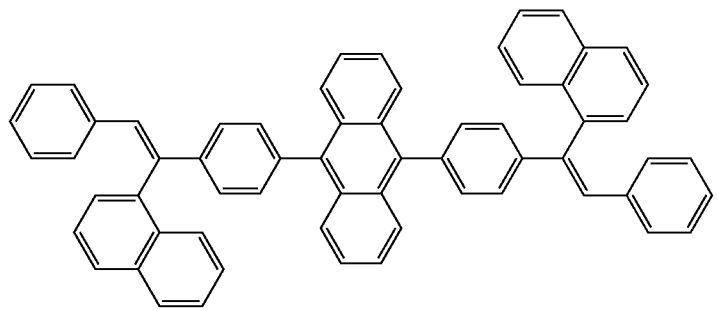

Formula 2c

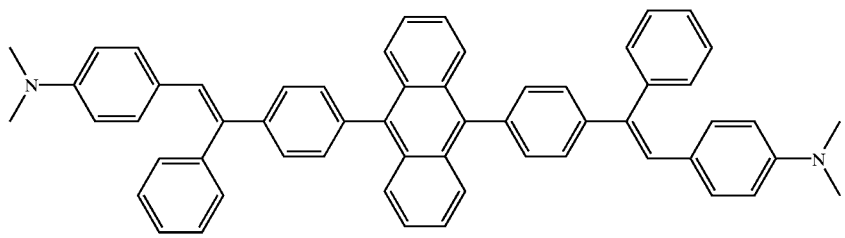

Formula 2d
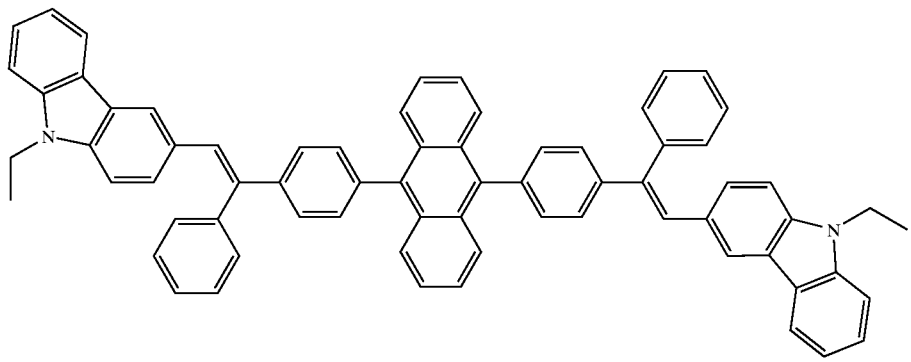
Formula 2e
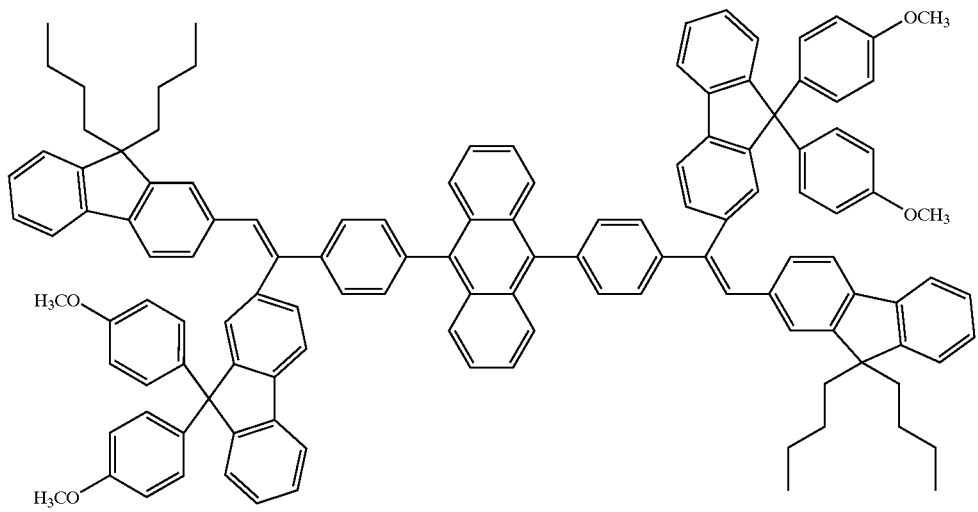
Formula 2f
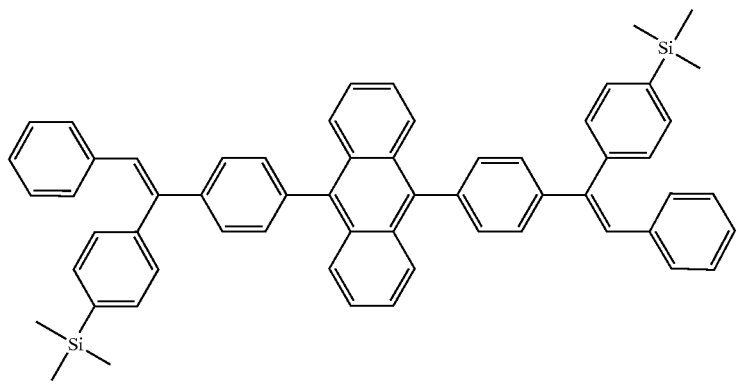

Compounds of the Formulae 2a to 2f having the above structures have styrly groups at both ends thereof and diphenylanthracene units at the center parts thereof, wherein phenyl groups substituted in the α-position of the styrly groups receive more steric hindrance compared phenyl groups substituted in the α-position of the styrly groups. Therefore, the band gap is increased so that the phenyl groups become a material which emits blue a lot, thereby obtaining superior color purity.

As the distortion is increased when the phenyl groups are substituted in the α-position of the styrly groups compared to phenyl groups substituted in the α-position of the styrly groups, π-stacking with an adjacent compound is hindered, and interaction of each of exitons is decreased. As a result, not only are high color purity and light emitting efficiency maintained, but also crytstallization is inhibited so that the stability of the thin film is greatly increased. Furthermore, hole transfer is easily accomplished due to the steric structure of the blue light emitting compounds according to the present invention.

A method for manufacturing an organic electroluminescent device according to the present invention is as follows.

FIG. 1 is a sectional view illustrating the structure of an ordinary organic electroluminescent device of the present invention.

First, an anode electrode (12) is formed by coating a material for the anode electrode on the upper part of a substrate (11), wherein a substrate used in an ordinary organic EL device is used as the substrate. Preferably a glass substrate or a transparent plastic substrate having superior transparency, surface flatness, easy handling property and waterproofing property is used.

Then, indium tin oxide (ITO), tin oxide ($SnO_2$), zinc oxide ($ZnO_2$), or the like, which are transparent and have superior conductivities, are used as the material for the anode electrode (12).

A hole transport layer (13) is formed by vacuum depositing or spin coating a material for the hole transport layer on the upper part of the anode electrode. The material for the hole transport layer (13) is not particularly limited, but can be N,N'-bis(3-methylphenyl)-N,N'-diphenyl-[1,1-biphenyl]-4,4'-diamine (TPD), N,N'-di(naphthalene-1-yl)-N,N'-diphenyl-benzidine (α-NPD), or the like.

Subsequently, an emitting layer (14) is formed by vacuum depositing one compound according to Formula 1 on the upper part of the hole transport layer (13).

Next, an organic EL device is completed by vacuum depositing a metal for forming a cathode on the upper part of the emitting layer (14), thereby forming a cathode electrode (16), wherein lithium (Li), magnesium (Mg), aluminum (Al), aluminum-lithium (Al—Li), calcium (Ca), magnesium-indium (Mg—In), magnesium-silver (Mg—Ag), or the like is used as a metal for forming the cathode.

An electron transport layer (15) can be formed on the upper part of the emitting layer (14) before the cathode electrode (16) is formed on the same, wherein a material for forming an ordinary electron transport layer is used as the electron transport layer(15).

An organic electroluminescent device of the present invention further comprises an intermediate layer which is formed between two layers selected from the anode electrode (12), the hole transport layer (13), the emitting layer (14), the electron transport layer (15) and the cathode electrode (16) for improving properties.

For example, a hole injection layer (HIL), which is not illustrated, can be further formed between the anode electrode (12) and the hole transport layer (13), wherein the formation of the hole injection layer not only improves adhesive strength between the hole transport layer (13), made of α-NPD for example, and the anode electrode (ITO) (12), but also facilitates the injection of a hole into the hole transport layer (13) from the anode electrode.

Although the material for forming the hole injection layer is not particularly limited, it can be selected from m-MTDATA, I-TNATA, and the like.

An organic electroluminescent device can be manufactured in the above described order of an anode, a hole transport layer, an emitting layer, an electron transport layer and a cathode, or in the reverse order of a cathode, an electron transport layer, an emitting layer, a hole transport layer and an anode.

Preferred examples of the present invention are offered as follows. However, the present invention is not limited to the following examples.

Synthetic Example 1

Preparation of a Compound of the Formula 2a

After dissolving 9,10-dibromoanthracene into dried diethylether using sodium, 2 equivalents of n-butyllithium were slowly added to the dissolved material at a temperature of −40° C. After stirring the reaction mixture at room temperature for 1 hour and cooling the reaction mixture to a temperature of −78° C. again, 5 equivalents of trimethylborate were added to the cooled reaction mixture before the mixture was stirred at room temperature for 10 hours. After slowly pouring the reaction mixture into a 4N—$H_2SO_4$ solution consisting of ice and sulfuric acid, the mixture was stirred for 2 hours so that compound (A) of the following Reaction Formula 1 was obtained, wherein the yield was 30%.

After dissolving compound (A) and 2 equivalents of 4-bromobenzophenone into tetrahydrofuran (THF), 0.6 to 1 mol % of tetrakis(triphenylphosphine)palladium and 2.5 equivalents of 2M—$K_2CO_3$ were added to the dissolved material. Compound (B) of the following Reaction Formula 1 was obtained by refluxing the reaction mixture for 24 hours, wherein the yield was 40%.

After preparing a Grignard reagent by reacting benzyl chloride with magnesium (Mg) for 2 hours under an anhydrous diethylether solvent, compound (B) was added to the Grignard reagent at room temperature. Then compound (C) of the following Reaction Formula 1 was obtained by refluxing the reaction compound for 5 hours, wherein the yield was 90%.

Figure 2:
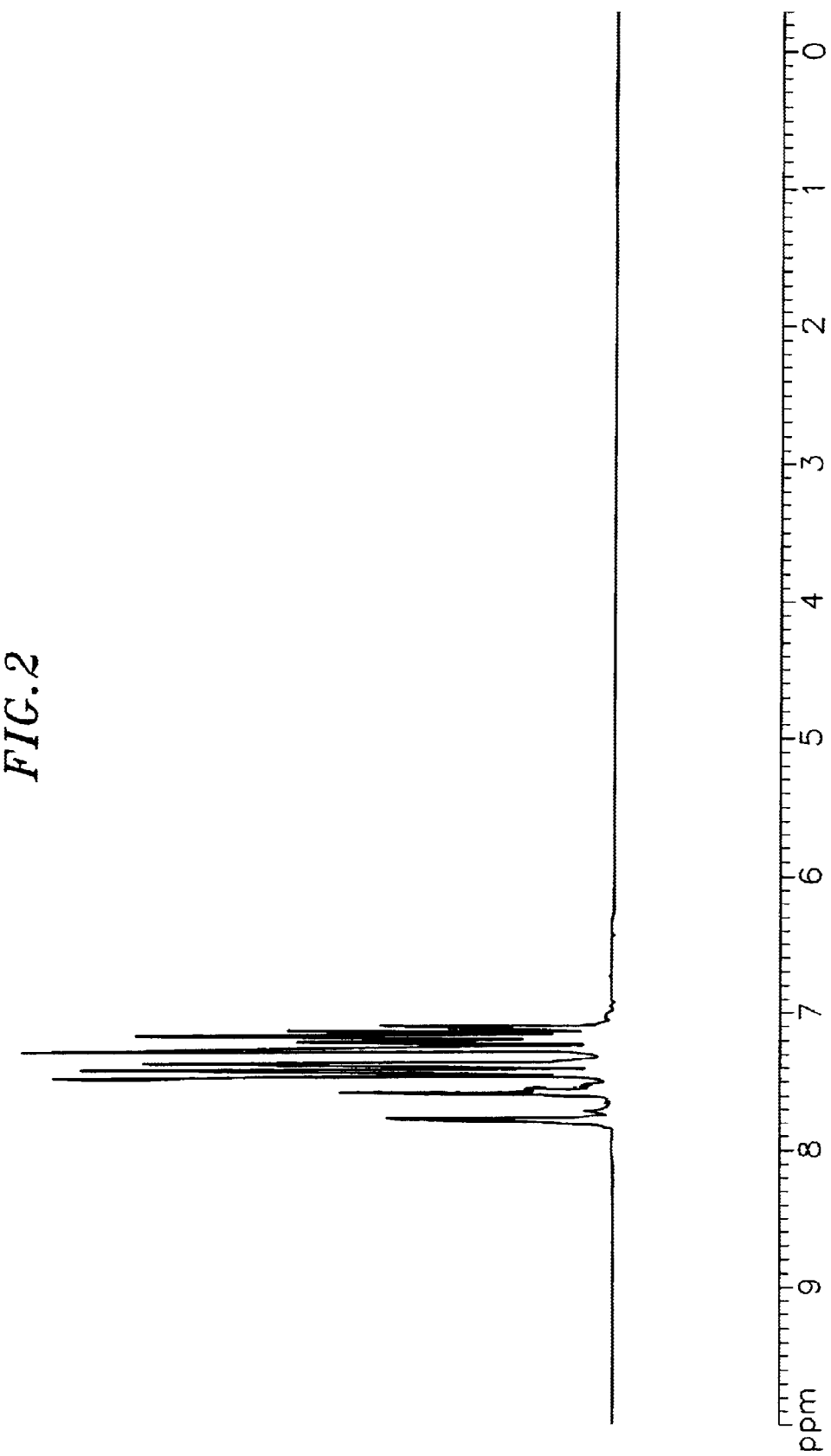
FIG. 2 is a graph illustrating an $^1$H-NMR spectrum of an electroluminescent polymeric compound represented by the following Formula 2a of the present invention.
Figure 3:
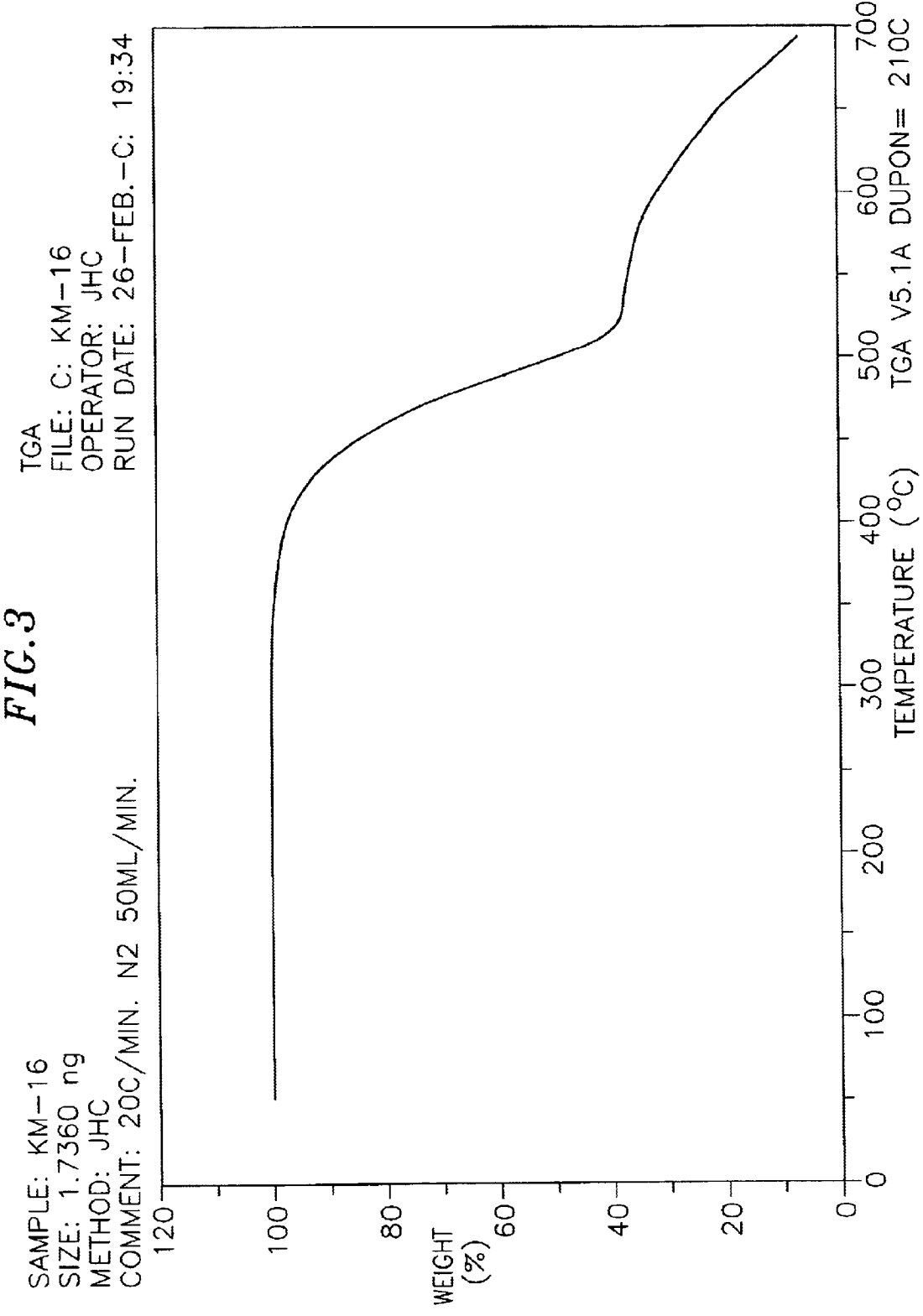
FIG. 3 is a graph illustrating a thermogravimetric curve of an electroluminescent polymeric compound represented by the following Formula 2a of the present invention.

A compound of the Formula 2a was obtained by refluxing compound (C) and p-toluenesulfonic acid (0.1 mol %) of catalyst amount in an excessive amount of benzene for 2 hours, wherein the yield was 97%. This was confirmed by the $^1$H-NMR spectrum illustrated in FIG. 2.

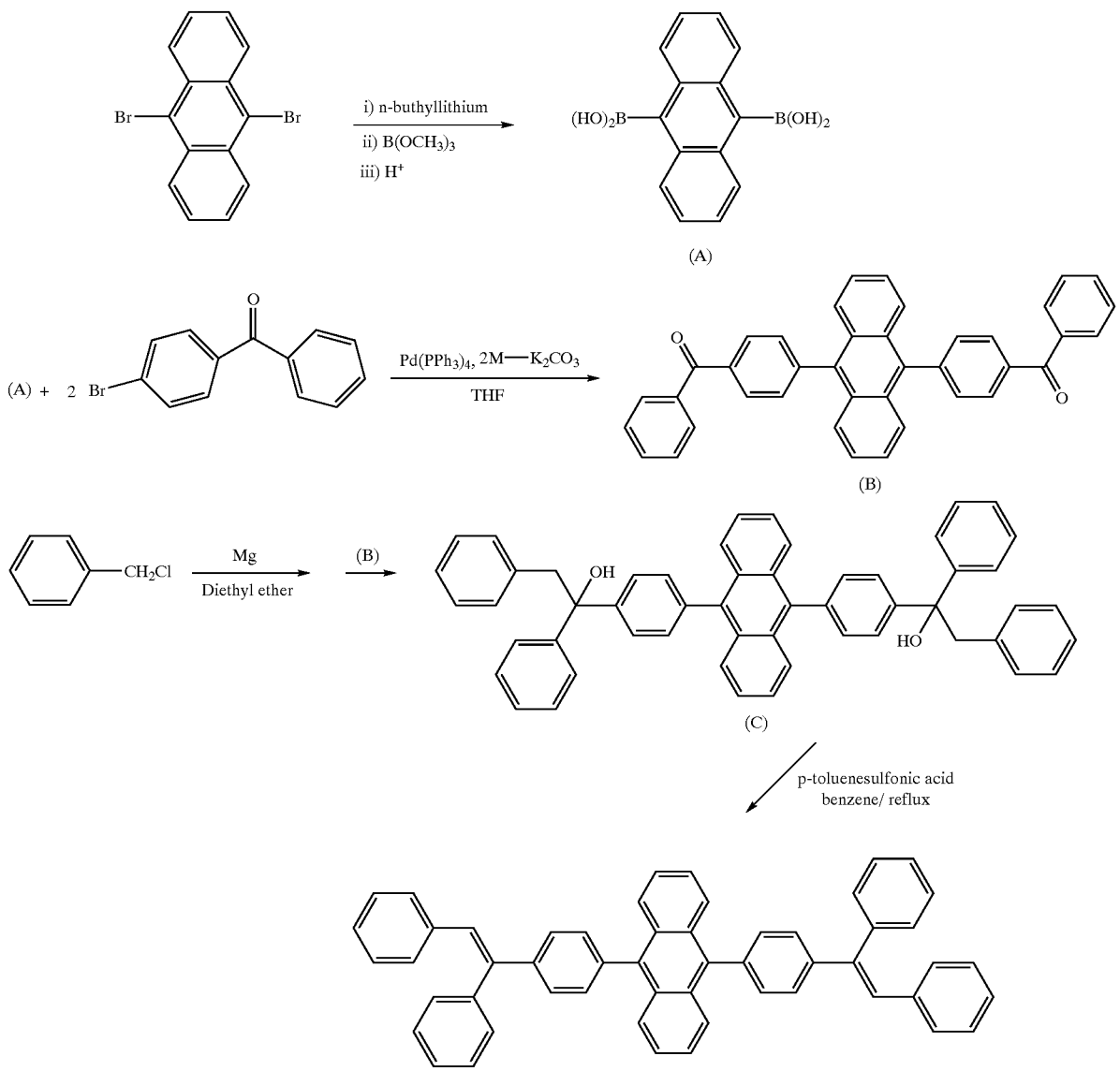

Manufacture of an Electroluminescent Device

EXAMPLE 1

A 10 Ω/cm² ITO substrate manufactured by Corning Corporation was used as an anode. A hole injection layer having a thickness of 500 Å was formed by vacuum depositing IDE 406 on the upper part of the substrate.

Subsequently, a hole transport layer with a thickness of 150 Å was formed by vacuum depositing a compound of the following Formula 3 on the upper part of the hole injection layer.

An emitting layer having a thickness of 300 Å was formed by vacuum depositing a compound of the Formula 2a on the upper part of the hole transport layer after forming the hole transport layer.

Subsequently, an electron transport layer having a thickness of 350 Å was formed by vacuum depositing a compound of the following Formula 4 on the upper part of the emitting layer. An organic electroluminescent device was manufactured as illustrated in FIG. 1 by sequentially vacuum depositing LiF with a thickness of 10 Å and Al with a thickness of 1500 Å on the upper part of the electron transport layer, thereby forming a LiF/Al electrode.

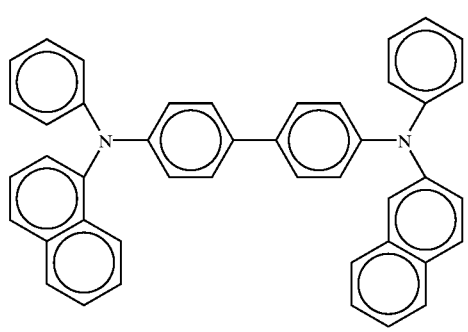

Formula 3

Formula 4

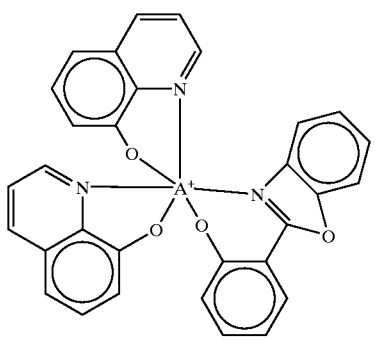

EXAMPLE 2

An organic electroluminescent device was manufactured by the same method as the Example 1 except that the compound of Formula 4 was vacuum deposited with a thickness of 450 Å instead of 350 Å.

EXAMPLE 3

An organic electroluminescent device was manufactured by the same method as the Example 2 except that the compound of Formula 2a was vacuum deposited with a thickness of 400 Å instead of 300 Å.

Comparative Example

An organic electroluminescent device was manufactured by the same method as the Example 1 except that a compound of an existing IDE 120 was used instead of the compound of Formula 2a.

The color characteristics of organic electroluminescent devices manufactured according to the Examples 1 to 3 and Comparative Example were examined and are shown in Table 1.

TABLE 1

| Classification | CIE | X, y |
|---|---|---|
| Example 1 | 0.15 | 0.10 |
| Example 2 | 0.15 | 0.12 |
| Example 3 | 0.15 | 0.15 |
| Comparative Example | 0.15 | 0.15 |

Figure 4:
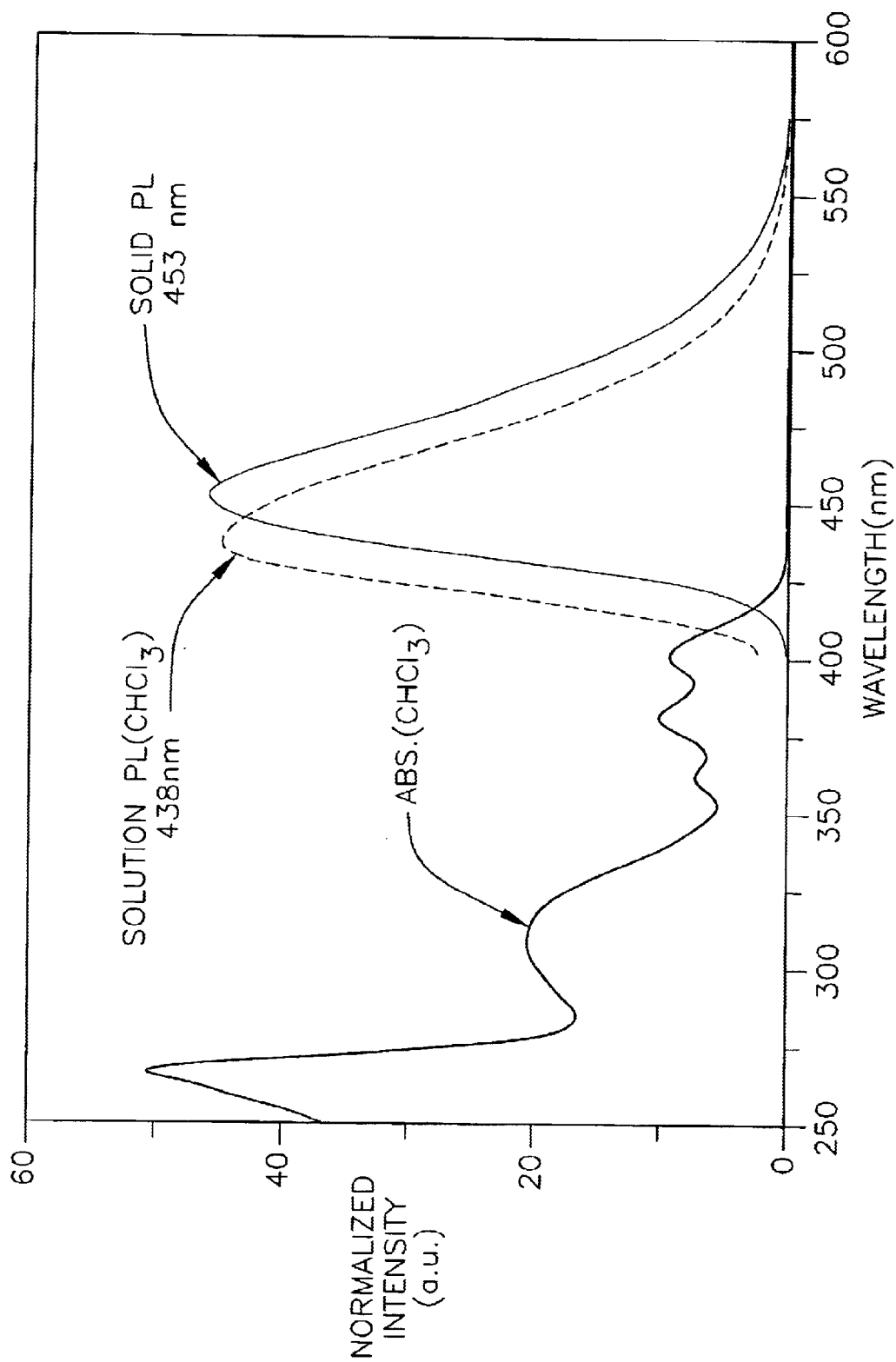
FIG. 4 is a graph illustrating an ultraviolet (UV) ray absorption and photoluminescence (hereinafter referred to as "PL") spectrum in the solution state and a PL spectrum in the film state of an electroluminescent polymeric compound represented by the following Formula 2a of the present invention.

It can be seen from Table 1 that organic electroluminescent devices according to Examples 1 to 3 produce blue colors having superior color purities and have better luminance properties compared with the organic electroluminescent device according to Comparative Example. Furthermore, as illustrated in FIG. 4, it can be seen that the wavelength in the solution state of a blue light emitting compound according to the Example 1 is 438 nm, while the wavelength in the film state of a blue light emitting compound according to the Example 1 is 453 nm. Therefore, it can be seen that the blue color having superior color purity is embodied.

As described in the foregoing, a compound of the Formula 1 according to the present invention has superior color purity as a blue light emitting material and useful as a color developing substance of a display device.

Furthermore, an organic electroluminescent device according to the present invention forms an organic film, such as an emitting layer, using a compound of the Formula 1, and improves stability of thin film and luminance properties compared to the use of an ordinary blue light emitting compound.

While the invention has been particularly shown and described with reference to preferred embodiments thereof, it will be understood by those skilled in the art that the foregoing and other changes in form and details may be made therein without departing from the spirit and scope of the invention.

What is claimed is:

1. A blue light emitting compound having the Formula 1:

Formula 1 wherein $Ar_1$ and $Ar_2$ are each independent substituents or substituent groups selected from the group consisting of aryl groups on which an aryl group, an alkyl group or an alkoxy group having 5 to 30 carbons may be substituted; fused aromatic ring groups having 4 to 24 carbons; aryl groups having 5 to 20 carbons as well as an alkyl amino group or an aryl amino group having 4 to 25 carbons; carbazole derivatives having an alkyl group or aryl group of 1 to 25 carbons; fluorenyl groups having a substituent on the C-9 position of the fluorenyl group selected from the group consisting of alkyl groups having 2 to 30 carbons, polyalkoxide groups, and alkyl or alkoxy substituted aryl groups.

2. A blue light emitting compound according to claim 1, wherein the x coordinate is 0.15 and the y coordinate ranges from 0.10 to 0.15 in a coordinate system of the blue light emitting compound.

3. A blue light emitting compound according to claim 1, wherein the blue light emitting compound is selected from the group consisting of compounds represented by the Formulae 2a to 2f:

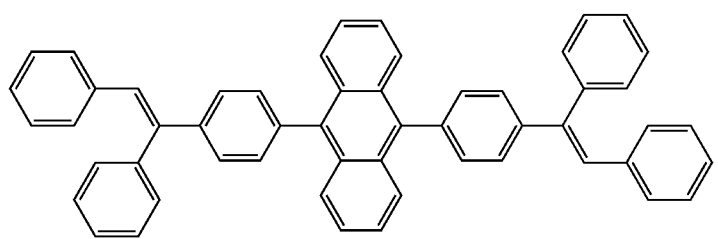
Formula 2a
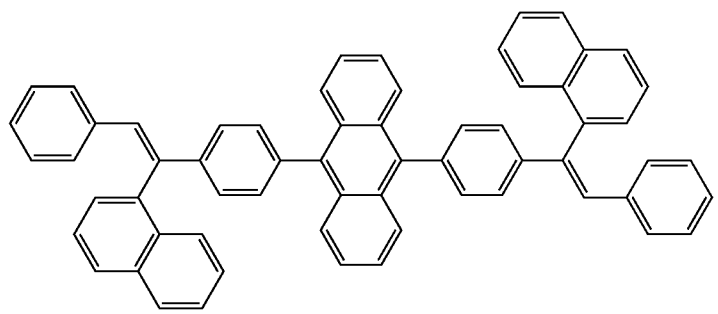
Formula 2b
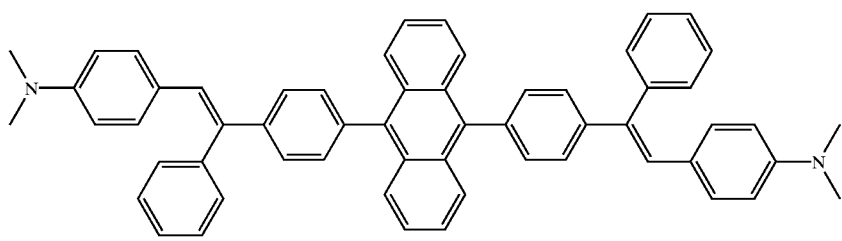
Formula 2c
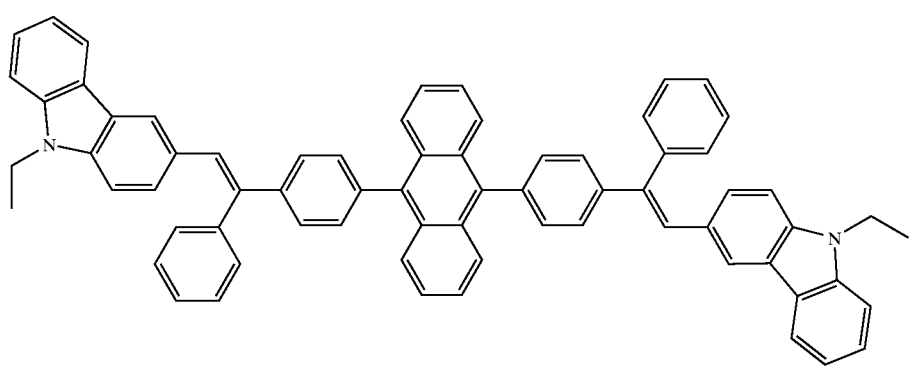
Formula 2d

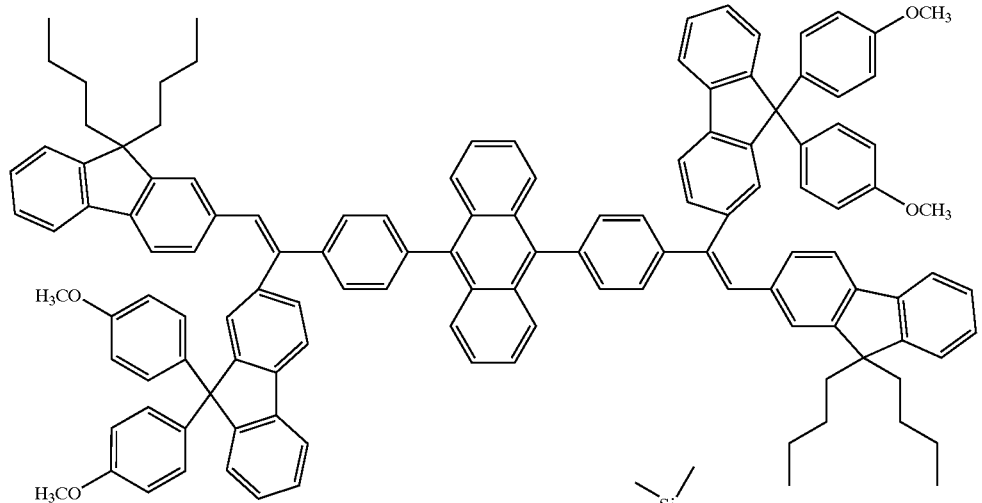

Formula 2e

Formula 2f

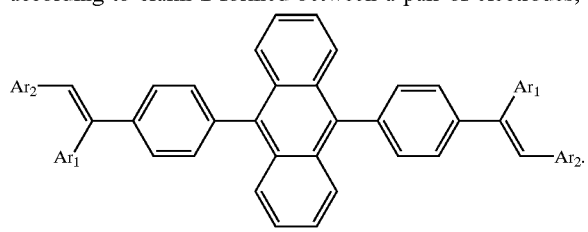

4. An organic electroluminescent device having an organic film comprising a blue light emitting compound according to claim 1 formed between a pair of electrodes,

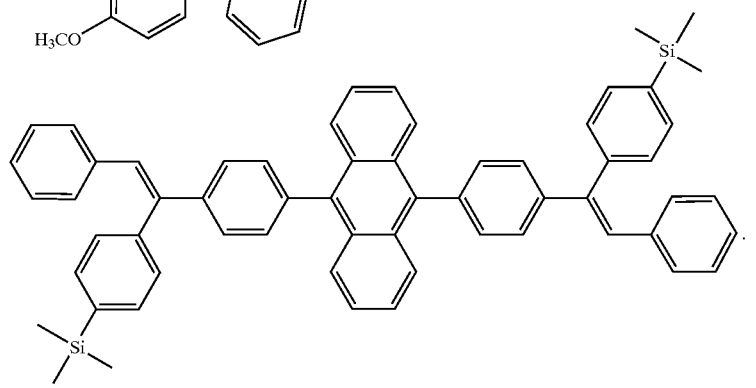

5. An organic electroluminescent device according to claim 4, wherein the blue light emitting compound has an x coordinate of 0.15 and a y coordinate ranging from 0.10 to 0.15.

6. An organic electroluminescent device according to claim 4, wherein the blue light emitting compound is selected from the group consisting of compounds represented by the Formulae 2a to 2f:

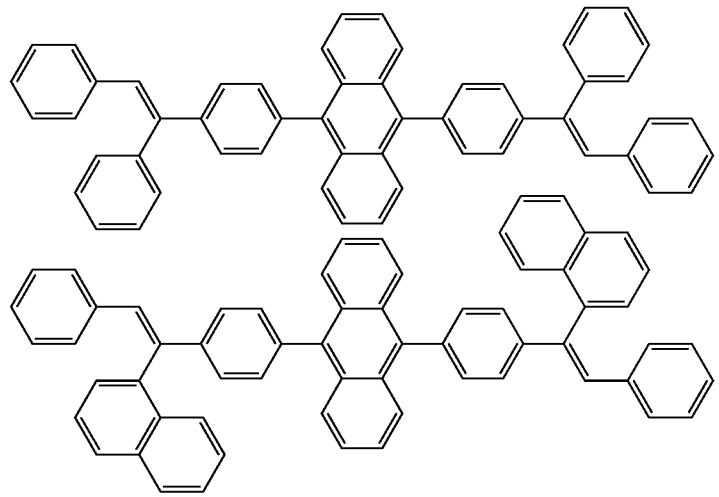

Formula 2a

Formula 2b

-continued

Formula 2c

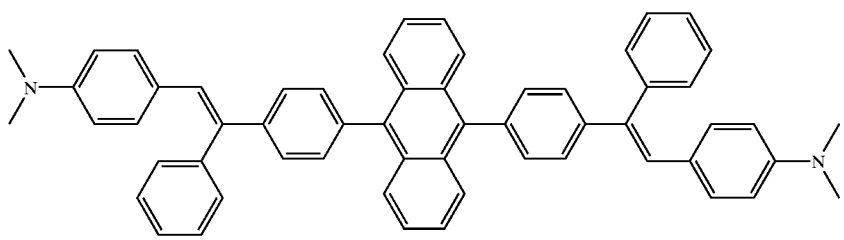

Formula 2d

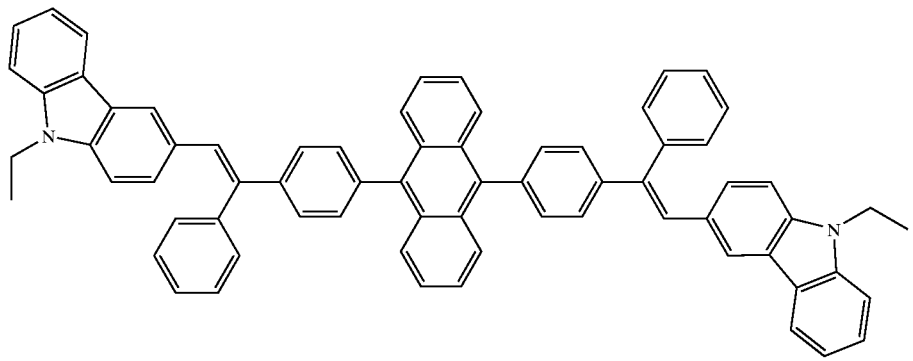

Formula 2e

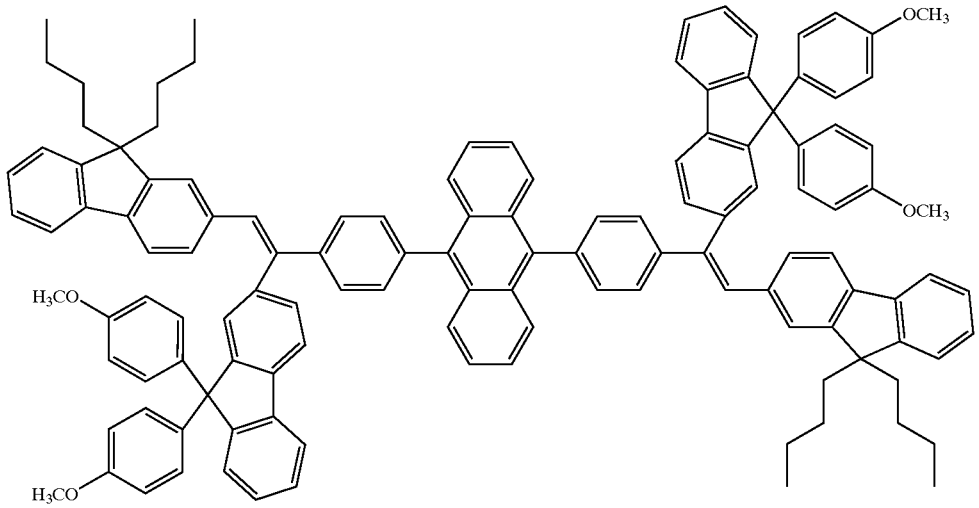

Formula 2f

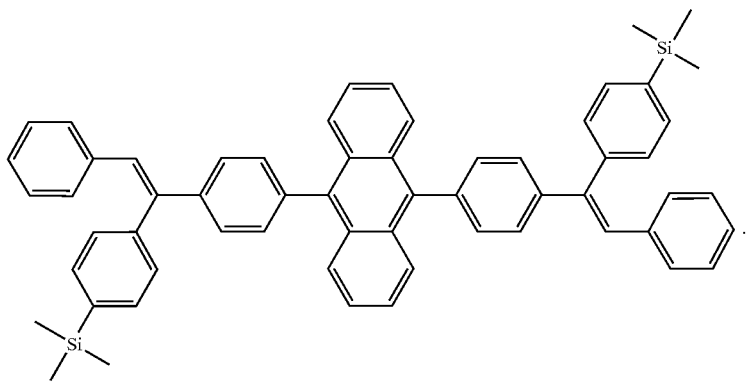

7. An organic electroluminescent device according to claim 4, wherein the organic electroluminescent device employs the light emitting compound as a host material.

8. An organic electroluminescent device according to claim 4, wherein the organic electroluminescent device further comprises a hole transfer material.

* * * * *